(12) United States Patent
Akeson et al.

(10) Patent No.: US 7,060,507 B2
(45) Date of Patent: Jun. 13, 2006

(54) TARGETED MOLECULAR BAR CODES AND METHODS FOR USING THE SAME

(75) Inventors: Mark Akeson, Santa Cruz, CA (US); David W. Deamer, Santa Cruz, CA (US); Wenonah Vercoutere, Santa Cruz, CA (US); Hugh E. Olsen, Santa Cruz, CA (US); Rebecca Braslau, Santa Cruz, CA (US); Bakthan Singaram, Santa Cruz, CA (US); Derek Steiner, Santa Cruz, CA (US); Frank Cappuccio, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 725 days.

(21) Appl. No.: 10/219,989

(22) Filed: Aug. 13, 2002

(65) Prior Publication Data

US 2006/0063196 A1    Mar. 23, 2006

Related U.S. Application Data

(63) Continuation of application No. 09/466,994, filed on Dec. 10, 1999, now Pat. No. 6,465,193.

(60) Provisional application No. 60/111,802, filed on Dec. 11, 1998, provisional application No. 60/158,020, filed on Oct. 6, 1999.

(51) Int. Cl.
*G01N 33/543* (2006.01)

(52) U.S. Cl. .............................. 436/518; 435/4; 435/6; 435/7.1; 436/501; 436/531; 436/532; 536/18.7; 536/22.1; 536/23.1

(58) Field of Classification Search ............ 435/4, 435/6, 7.1; 436/501, 518, 531, 532; 536/18.7, 536/22.1, 23.1
See application file for complete search history.

(56) References Cited

U.S. PATENT DOCUMENTS

| | | | | |
|---|---|---|---|---|
| 5,258,506 A | * | 11/1993 | Urdea et al. | ............... 536/23.1 |
| 5,573,905 A | | 11/1996 | Lerner et al. | |
| 5,723,598 A | | 3/1998 | Lerner et al. | |
| 5,854,033 A | * | 12/1998 | Lizardi | ..................... 435/91.2 |
| 5,986,076 A | * | 11/1999 | Rothschild et al. | ........ 536/22.1 |

FOREIGN PATENT DOCUMENTS

| EP | 394997 | 10/1990 |
|---|---|---|
| EP | 698792 | 2/1996 |
| EP | 0698792 | * 2/1996 |

(Continued)

OTHER PUBLICATIONS

Akeson, et al., "Microsecond Time-Scale Discrimination Among Polycytidylic Acid, Polyadenylic Acid, and Polyuridylic Acid as Homopolymers or as Segments Within Single RNA Molecules" Biophysical Journal Dec. 1999, (V 77), 3227-3233.

(Continued)

*Primary Examiner*—Christopher L. Chin
(74) *Attorney, Agent, or Firm*—Bret E. Field; Bozicevic, Field & Francis LLP

(57) ABSTRACT

Targeted molecular bar codes and methods for using the same are provided. The subject targeted molecular bar codes include a molecular bar code and a member of a specific binding pair, where the specific binding pair member is generally bonded to the bar code through a linking group. The subject molecular bar code may be read during translocation through a single nano-meter scale pore. The subject targeted molecular bar codes find use in a variety of different applications involving analyte detection, such as screening and diagnostic applications.

28 Claims, 13 Drawing Sheets

FOREIGN PATENT DOCUMENTS

| | | | |
|---|---|---|---|
| WO | WO9426932 | * | 11/1994 |
| WO | WO 95/08637 | | 3/1995 |
| WO | WO 96/12014 | | 4/1996 |
| WO | WO 97/20203 | | 6/1997 |
| WO | WO 98/55657 | | 12/1998 |

OTHER PUBLICATIONS

Dell'Aquila, et al., "Photolabile Linker for the Solid Phase Synthesis of Base-Sensitive Oligonucleotides," Tetrahedron, 1997, No. 30 (V38), pp. 5289-5292.

Kasianowicz, et al., "Characterization of Individual Polynucleotide Molecules Using a Membrane Channel," Proc. Natl. Acad. Sci. USA, Nov. 1996 (V93), pp. 13770-13773.

Wonderlin, et al., "Optimizing Planar Lipid Bilayer Single-Channel Recordings for High Resolution with Rapid Voltage Steps," Biophys J., Aug. 1990 (V58) pp. 289-297.

Ohlmeyer et al. (1993). "Complex synthetic chemical libraries indexed with molecular tags" *Proc. Natl. Acad. Sci. USA*, vol. 90: 10922-10926.

* cited by examiner

A) Control

—120 pA

— 0 pA

B) 18mer polydT, 20 uM

←———— 1 Second ————→

Blockade Duration

500 μs

Neutral Hydrophilic Monomers homopolymer  random copolymer  gradient copolymer  block copolymer

SEQUENCE LISTING

<160> NUMBER OF SEQ ID NOS: 2

<210> SEQ ID NO 1
<211> LENGTH: 132
<212> TYPE: DNA
<213> ORGANISM: Artificial
<220> FEATURE:
<223> OTHER INFORMATION: artificial oligonucleotide

<400> SEQUENCE: 1
taatacgact cactataggg aaaaaaaaaa aaaaaaaaa aaaaaaaaa cccccccccc      60 cccccccccc cccccccccc cccccccccc cccccccccc cccccccccc cccccccccc   120
ggtaccacac ac                                                       132

<210> SEQ ID NO 2
<211> LENGTH: 137
<212> TYPE: DNA
<213> ORGANISM: Artificial
<220> FEATURE:
<223> OTHER INFORMATION: artificial oligonucleotide
<220> FEATURE:
<221> NAME/KEY: modified_base
<222> LOCATION: (1)..(20)
<223> OTHER INFORMATION: 5-nitroindole
<220> FEATURE:
<221> NAME/KEY: modified_base
<222> LOCATION: (31)..(31)
<223> OTHER INFORMATION: dT
<220> FEATURE:
<221> NAME/KEY: modified_base
<222> LOCATION: (21)..(30)
<223> OTHER INFORMATION: Spacer9
<220> FEATURE:
<221> NAME/KEY: modified_base
<222> LOCATION: (31)..(39)
<223> OTHER INFORMATION: Spacer9
<220> FEATURE:
<221> NAME/KEY: modified_base
<222> LOCATION: (40)..(40)
<223> OTHER INFORMATION: dT

<400> SEQUENCE: 2
nnnnnnnnnn nnnnnnnnnn nnnnnnnnnn tnnnnnnnnt tttttttttt ttttttttcta    60 gagcgctttg cgctctagac cccccccccc ccccccgtg tccaatgaca acgatgttga    120
tgtgagtctt ttcctttt                                                 137

TARGETED MOLECULAR BAR CODES AND METHODS FOR USING THE SAME

CROSS-REFERENCE TO RELATED APPLICATIONS

This application is a continuation of U.S. application Ser. No. 09/466,994, filed Dec. 10, 1999 and now issued as U.S. Pat. No. 6,465,193, which claims priority to the filing date of the U.S. Provisional Patent Application Ser. No. 60/111,802 filed Dec. 11, 1998 and U.S. Provisional Patent Application Ser. No. 60/158,020 filed Oct. 6, 1999, the disclosures of which are herein incorporated by reference.

ACKNOWLEDGMENT

This invention was made with United States Government support under Grant Nos. HG/OD 01360-01 and HGO 1826-01B awarded by the NIH. The United States Government has certain rights in this invention.

INTRODUCTION

1. Field of the Invention

The field of this invention is analyte detection, particularly labels employed in analyte detection.

2. Background of the Invention

Analyte detection, in which a sample is assayed for the presence of a particular analyte of interest, is critical to a variety of fields. For example, analyte detection protocols are employed in the characterization of complex mixtures, the identification and characterization of novel compounds of interest, and the like, both in industry and academia. Analyte detection also plays a role in medicine, particularly in the diagnosis of disease. In such applications, a sample from a patient is assayed for the presence of one or more specific analytes indicative of the disease being diagnosed. Environmental monitoring applications, such as the monitoring of pollutants and toxins, also employs analyte detection protocols.

Where an analyte of interest is not readily measured directly, the use of a detectable label is required. A variety of detectable labels have been developed over the years for use in analyte detection. These include both directly and indirectly detectable labels. Directly detectable labels include radioisotopes, enzymes, fluorescent and chemiluminescent agents, or other labels capable of being directly detected. Where an indirectly detectable label is employed, it is generally a member of a signal producing system such as a second stage antibody or reagent that is used to amplify the signal. Such reagents are well known in the art. For example, the primary antibody may be conjugated to biotin, with horseradish peroxidase-conjugated avidin added as a second stage reagent. Alternatively, the secondary antibody may be conjugated to a fluorescent compound, e.g. fluorescein, rhodamine, Texas red, etc. Final detection uses a substrate that undergoes a color change in the presence of the peroxidase.

Despite the wide variety of different labeling agents that have been developed over the years for use in analyte detection, there is still an interest in developing new ones. Of particular interest would be the development of sensitive labels that can simultaneously detect small quantities of analytes present in complex mixtures by methods that do not require preparation steps prior to detection.

Relevant Literature

U.S. patents of interest include: U.S. Pat. Nos. 5,573,905 and 5,723,598. Also of interest are Akeson et al., "Microsecond time-scale discrimination between polycytidylic acid, polyadenylic acid and polyuridylic acid as homopolymers or as segments within single acid as homopolymers or as segments within RNA molecules" Biophys. J (1999) 77:3227–3233; Wonderlin et al., "Optimizing planar lipid bilayer single-channel recordings for high resolution with rapid voltage steps" Biophys. J.(1990) 58:289–297; and Kasianowicz, et al., "Characterization of individual polynucleotide molecules using a membrane channel," Proc. Natl. Acad. Sci. USA (1996) 93: 13770–13773. See also, Benoit et al., J. Am. Chem. Soc. (1999) 121:3904; Hawker et al., Paper 136, PMSE Division, 217th ACS Meeting, Anaheim (1999); Hawker et al., Acc. Chem. Res. (1997) 30:373; Dao et al., J. Polymer Science Part A-Polymer Chemistry (1998) 36:2161–2167; Keck et al., J. Org. Chem. (1996) 61:359.

SUMMARY OF THE INVENTION

Targeted molecular bar codes and methods for their use in analyte detection are provided. The subject targeted molecular bar codes comprise a molecular bar code bonded to a member of a specific binding pair, usually through a linking group. The molecular bar codes are charged polymeric compounds, preferably negatively charged compounds, e.g. negatively charged block copolymers, that can be detected by a nanopore. The subject targeted molecular bar codes find use in a variety of different analyte detection applications, including screening and diagnostic applications.

DETAILED DESCRIPTION OF THE INVENTION

Figure 1:
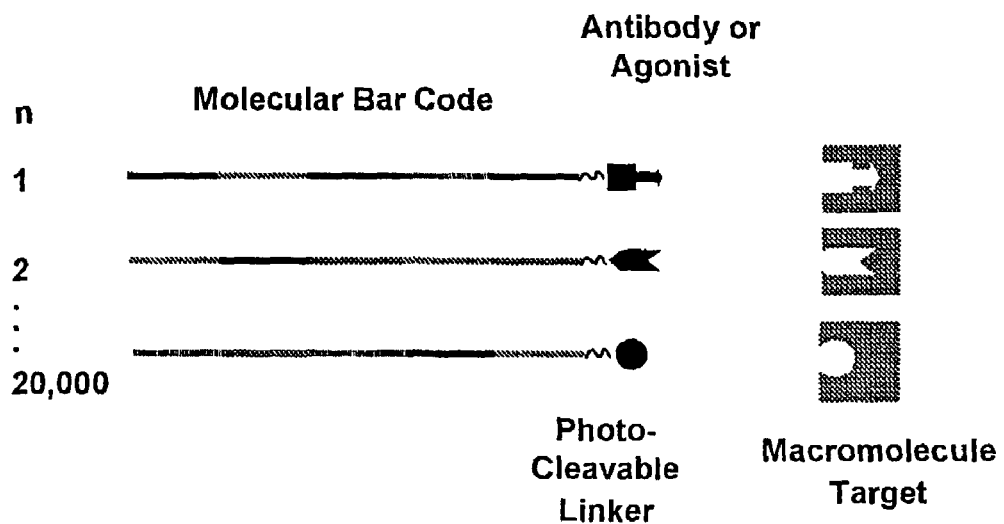
FIG. 1 provides a schematic diagram of a targeted molecular bar code.

Targeted molecular bar codes and methods for their use in analyte detection are provided. The subject targeted molecular bar codes include a molecular bar code stably associated with, e.g. covalently attached, typically through a linking group, to a member of a specific binding pair (see FIG. 1). The molecular bar code is generally a charged polymeric compound, and in preferred embodiments, is a negatively charged or anionic compound, e.g. a negatively charged block copolymer. The subject targeted molecular bar codes find use in a variety of different analyte detection applications, including screening and diagnostic applications. In further describing the subject invention, the targeted molecular bar codes will be described first followed by a discussion of methods for their use in analyte detection.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Figure 2:
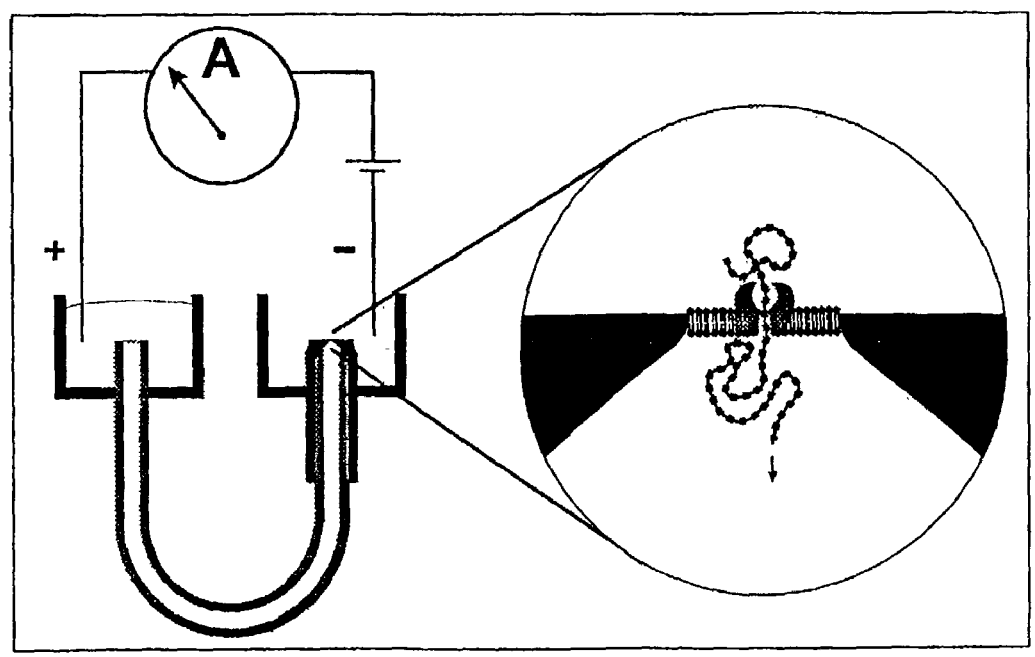
FIG. 2 provides a schematic of a nanopore device that may be used to examine molecular bar codes.

A critical feature of the targeted molecular bar code of the subject invention is the molecular bar code. The molecular bar code is a polymeric molecule that is capable of being translocated through a nanopore under the influence of an applied electric field (see FIG. 2). Importantly, during translocation of the molecular bar code through the nanopore, a reproducible signal is produced, for example a current blockade profile (see FIG. 3). Other signals may include fluorescence, chemiluminescence, or variations in tunneling current. By current blockade profile is meant the collection of current blockade data points plotted versus a given period of time upon application of an applied electric field to a nanopore. Components of the profile that may be employed include one or more of amplitude, duration and pattern, where usually two or more of these characteristics are detected when looking at the current blockade profile. The given period of time that a single bar code molecule is examined is generally at least about 10 microseconds, usually at least about 100 microseconds and more usually at least about 250 microseconds, and may be as long as 10 milliseconds or longer, but will usually not exceed about 5 milliseconds in length. The current blockade data points are derived from the observed change in ionic current through the nanopore from the cis to the trans side upon occupancy by the polymeric molecular bar code. Suitable current measurement devices, as well as hardware and software necessary for generating the current blockade profile from the observed changes in current, are well known to those of skill in the art and a representative system is disclosed in the Experimental Section, infra.

The polymeric molecular bar code is sufficiently long to generate a distinctive, reproducible signature or current blockade profile such that the molecular bar code provides a distinctive tag for the specific binding member with which it is associated, (e.g. covalently attached) in the targeted molecular bar code. As such, the length of the polymeric molecular bar code is at least about 10 nm, usually at least about 20 nm and more usually at least about 50 nm, where the length may be as long as 1000 nm or longer, but will usually not exceed about 500 nm and more usually will not exceed about 400 nm. The polymeric molecular bar code is either a linear or non linear, e.g. branched polymer, where non-linear polymers of interest include comb polymers, star polymers, and dendritic polymers. In many embodiments, the polymer is generally a linear molecule. The linear polymeric molecule may or may not assume a secondary structure under the conditions in which it is employed, e.g. physiologically acceptable aqueous solutions, where the secondary structure may be a helical configuration, a loop, e.g a hairpin loop, etc. The only limitation with respect to the physical dimensions of the molecular bar code is that it be able to assume a configuration that allows it to pass or translocate lengthwise through the nanopore from the cis side to the trans side.

The polymeric molecular bar code is generally a charged molecule such that it moves under the influence of an applied electric field. While in the broadest sense the molecular bar code may be positively or negatively charged, it is generally negatively charged. In other words, the molecular bar code is typically an anionic polymeric molecule.

The molecular bar code may be a homopolymer or a copolymer of two or more different types of monomers. As indicated above, the only limitation on the molecular bar code is that it generate a distinct and reproducible signal upon translocation through a nanopore, as described in greater detail infra. Block copolymers of interest include polymers of 2 or more up to 10 or more different types of monomeric units, where copolymers of interest include random, gradient and block copolymers.

In many embodiments of interest, the molecular bar code is a block copolymer in which a plurality of blocks are covalently bonded to each other in sequential fashion. By plurality of blocks is meant at least 2, where the block copolymer will generally have from 2 to 20 blocks, usually from 2 to 10 blocks and in many cases from 3 to 10 blocks. In the molecular bar codes, the number of unique blocks may be the same as the total number of blocks in the copolymer or it may be less, e.g. in molecular bar codes in which a given unique block is repeated one or more times. In many preferred embodiments, the total number of distinct blocks in the copolymer is less than the total number of blocks in the polymer. In these preferred embodiments, the total number of distinct blocks in any given copolymer will generally range from 1 to 6, and usually from 2 to 4, with 3 distinct blocks being found in many molecular bar codes of particular interest.

Each block in the polymer may be heteropolymeric or homopolymeric. As such, each block in the polymer may be made up of the same monomeric units or a plurality of different monomeric units. Where the block is a heteropolymer made up of a plurality of monomeric units, the number of different monomeric units is at least 2, and may be as high as 5 or 7 or more, but is generally not more than 4. In many embodiments, the heteropolymeric block is a polymer of 2 or 3 different monomeric units.

The length of each block within a molecular bar code will be sufficient to generate a reproducible current blockade or other signal as the block translocates through a nanopore under an applied electric field. As such, the length of each block will generally range from about 1 or 5 to 50, usually from about 5 or 10 to 30 and more usually from about 10 or 15 to 20 or 25 nm, where in many embodiments the length will be about 15 to 20 nm. Depending on the nature of the monomeric units of the block, the number of monomeric units in a particular block may vary, where the number of monomeric units in a block will range from about 1 to 100, usually from about 3 to 60 and more usually from about 5 to 40.

In many preferred embodiments, the block(s) of the negatively charged or anionic polymeric bar codes are homopolymers of monomeric units that include a phosphate group (or phosphorothioate group), where the phosphate group (or phosphorothioate group) is not a pendant group but a member of the polymeric backbone of the bar code, i.e. the backbone of the polymer includes the presence of phosphodiester bonds. Of particular interest as monomeric units are phosphates or sugar phosphates. When the monomeric units are sugar phosphates, the sugar moiety of the monomeric unit will generally be from 4 to 6 carbon atoms, where the carbon atoms will generally form a cyclic structure, e.g. a pentose or hexose. Of particular interest are 6 carbon sugars forming a five-sided ring structure, specifically ribose and deoxyribose. The monomeric units may further include one or more pendant groups, such as heterocyclic nitrogenous bases, e.g. purines and pyrimidines. Specific purines of interest include naturally occurring and synthetic purines, where naturally occurring purines such as adenine and guanine, specifically adenine, are of particular interest. Likewise, specific pyrimidines of interest include naturally occurring and synthetic pyrimidines, where naturally occurring pyrimidines such as cytosine, thymine and uracil, particularly uracil and cytosine, are of particular interest. In many embodiments, the purines and pyrimidines are modified to minimize hydrogen bonding between pairs, e.g. Watson-Crick base-pairing is minimized.

The block(s) of the molecular bar code are, in many embodiments, homopolymers of monomeric units having the structural formula:

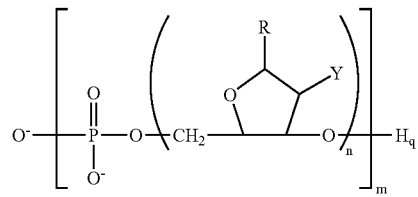

wherein:
R is H or a heterocyclic nitrogenous base, e.g. a heterocyclic nitrogenous base that may or may not be capable of participating in Watson-Crick base pairing interactions, such as a purine or a pyrimidine;
Y is H or OH;
n is 0 or 1;
m is an integer ranging from 10 to 80; and
q is 0 or 1.

Specific polymeric blocks of interest include: polycytidylic acid, polyadenylic acid, polyuridylic acid, polyphosphate, oligodeoxyribose phosphate (i.e. abasic polydeoxyribose phosphate), polyethylene glycol-phosphodiesters, oligonucleotides (including modified oligodeoxynucleotides such as oligo-5-nitroindole that do not form Watson-Crick base pairs), polystyrenes, polyacrylic acids, polyacrylates, polyacetonitriles, polyvinylphosphonates, polyacetamides and the like. Of particular interest in certain embodiments are molecular bar codes that are fabricated from polymers with biologically inert backbones, where such polymers include polystyrenes, polyacrylic acids, polyacrylates, polyacetonitriles, polyvinylphosphonates, polyacetamides and the like.

In many embodiments, the polymeric compound that is the molecular bar code is not a deoxyribonucleic acid in which all of the bases are selected from the group containing adenine, cytosine, thymine, and guanine bases. For example, where one of the blocks of a copolymer is an oligodeoxyribonucleotide comprised of one of these bases, the molecular bar code will usually comprise at least one additional non-oligodeoxyribonucleotide, such as polyacrylic acid, polystyrene, polyacetamides, polyphosphate, oligodeoxyribosephosphate, etc. Accordingly, the entire molecular bar code will not be a deoxyribonucleic acid in these particular embodiments.

To further modify the properties of the molecular bar code, e.g. the profile of the bar code generated upon translocation through a nanopore, a number of different types of elements can be incorporated into the bar codes. For example, secondary structures may be built into the bar code, as mentioned above. Of particular interest in certain embodiments are hairpin structures, which may be built into the bar code to modulate the profile generated by the bar code, extend the translocation time of the barcode through the pore, etc.

Hairpin structures form when a single polymer contains regions of complementary sequence separated by several non-complementary units. The polymer strand folds on itself so that the complementary regions associate, forming the stem of the hairpin. The non-complementary units connecting the complementary regions form a loop. Hairpin stem structures of interest vary in length from about 1 to 24 bp, but typically range from about 2 to 12 and usually from about 2 to 10 bp in length. As such, the length of the polymeric stretch that gives rise to the hairpin under the conditions of use of the bar code typically ranges in certain embodiments from about 36 to 94 monomers, usually from about 36 to 68 monomers and more usually from about 56 to 64 monomers; while in other embodiments from about 6 to 52 monomers, usually from about 8 to 28 monomers and more usually from about 8 to 24 monomers. The polymeric stretch or domain may be made up of any sequence of monomeric residues, where the residues may be naturally occurring or synthetic residues (i.e. non-naturally occurring residues) so long as a portion of the residues, generally the residues at either end of the polymeric domain, are capable of hybridizing to each other analogous to a Watson-Crick base pair type interaction. In other words, the polymeric domain that gives rise to the hairpin loop has two flanking regions that are complementary to each other, where the length of each complementary flanking region in terms of monomeric units ranges in length from about 1 to 24 units, usually from about 2 to 12 units and more usually from about 2 to 10 units. As such, the residues are typically nucleotides, either naturally occurring or synthetic. Separating the flanking residues that participate in the base pairing interaction described above to form the hairpin loop structure is a domain of residues that do not participate in hybridization but serve as a spacer group. Generally, the length of this spacer group in terms of monomeric units ranges from about 1 to 6 units, usually from about 2 to 5 units, and more usually from about 3 to 4 units.

Specific bar codes of interest include: polycytidylic acid, polyadenylic acid, polyuridylic acid, polyA/polyC block copolymers, polyC/polyU block copolymers, polydT comprised of 5 to 150 monomers, random DNA oligonucleotides, abasic deoxyribose-phosphate polymers, DNA or non-DNA polymers containing base-paired hairpins, DNA hairpins, polyacrylic acids, polyacetamides, polyacrylates, and polystyrenes.

Stably associated with, and preferably covalently attached to, the molecular bar code of the targeted molecular bar code, is the second requisite moiety—the member of a specific binding pair. The specific binding pair member may be attached either directly to the molecular bar code or, preferably, through a linking group, more particularly a cleave-able linking group. By cleave-able linking group is meant that the linking group can be cleaved under conditions that do not disrupt, e.g. hydrolyze, the molecular bar code but serve to release the entire molecular bar code from the specific binding pair member of the targeted molecular bar code. Preferably, linkers are those that can be incorporated into the synthesis of the barcode, even where automated synthesis protocols are employed. The linking group may be a variety of different moieties, where suitable groups include: disulfide groups, restriction sites, photocleavable groups, and the like. Chemically cleavable linkers of interest are those that include disulfide groups, dimethoxytrityl groups, etc. Restriction sites of interest that may be present in the linking groups include: EcoR I, Sma I, Kpn I, Dra I and the like. Photocleavable groups of interest include: vanillin based photolabile linkers, and the like.

The specific binding pair member may be any moiety capable of specifically interacting with a second moiety, e.g. an analyte of interest. As such, the specific binding pair member of the targeted molecular bar code may be a ligand or receptor, an antibody or binding fragment thereof, e.g. Fv, $F(ab)_2$ and Fab, an antigen recognized by a circulating antibody and the like; a nucleic acid, e.g. oligonucleotide, etc., where the nature of the specific binding pair member will depend on the nature of the analyte of interest, e.g. whether the analyte is a receptor or other cell surface antigen, a ligand, RNA, DNA, etc. In some cases the polymer portion of the targeted molecular bar code may serve as the second requisite moiety, i.e. the specific binding pair that binds with the analyte.

The subject targeted molecular bar codes can be fabricated using any convenient protocol, where a variety of protocols are known to those of skill in the art. For example, the polymeric molecular bar code can be synthesized in whole or in parts, where the parts are subsequently joined together. The resultant polymeric molecular bar code can then be conjugated to the binding moiety to produce the targeted molecular bar code. The manner by which the targeted molecular bar code is produced is not critical to the invention. The particular method employed will depend, at least in part, on the nature of the targeted molecular bar code and its constituent parts. For example, for those components of the bar code that are nucleic acids, chemical synthesizers and/or recombinant techniques may be employed. For those components that are biologically inert polymers, e.g. polystyrenes, polyacrylates, etc., synthetic polymerization protocols can be employed, where of particular protocols of interest are living polymerizations that yield products of low polydispersity and controlled molecular weights, e.g. as reported in Benoit et al., J. Am. Chem. Soc. (1999) 121: 3904. Representative procedures for producing targeted molecular bar codes is provided in the experimental section, infra.

The subject targeted molecular bar codes find use in a variety of applications, particularly analyte detection applications in which a sample is assayed for the presence of an analyte(s) of interest. A wide variety of analytes may be detected using the subject targeted molecular bar codes, where such analytes include both naturally occurring and synthetic compounds, e.g. biological analytes, such as antibodies, receptors, ligands, peptides, proteins, nucleic acids (DNA, RNA), viruses, bacteria, toxins, etc.; and environmental analytes, e.g. toxins, pollutants, etc.; and the like.

The sample that is screened in the subject methods may be obtained from a variety of sources. Samples, as used herein, include biological fluids such as blood, cerebrospinal fluid, tears, saliva, lymph, dialysis fluid, semen and the like; organ or tissue culture derived fluids; food and fluids extracted from cells or physiological tissues, where the cells may be dissociated, in the case of solid tissues, or tissue sections may be analyzed. Alternatively a lysate of the cells may be prepared. Other samples of interest include environmental samples, such as plant tissue samples, ground water samples, soil samples, and derivatives of such samples. Because of the nanoscale dimensions of the poer detector, the sample that is screened may be as small as a single biological cell (typically of 10 μm diameter) or as small as a defined target within a biological cell such as organelles, vescicles etc. (typically of 1 μm diameter or less).

In performing the subject methods of analyte detection, the first step is to contact the sample suspected of comprising the analyte of interest with a targeted molecular bar code having a specific binding pair member specific for the analyte of interest. The term "contact" is used in the broadest sense to mean any type of combining action which brings the targeted molecular bar into sufficiently close proximity with the analyte of interest in the sample such that a binding interaction will occur if the analyte of interest specific for the specific binding pair member of the targeted bar code is present in the sample. Contacting can be achieved in a variety of different ways, including introducing the targeted molecular bar code into the sample, and the like.

Following contact or introduction of the targeted molecular bar code into the sample, the resultant reaction mixture is incubated for a sufficient period time for any specific binding interactions, e.g. ligand-receptor binding, hybridization, etc., between the specific binding pair member and analyte (if present) in the sample to occur. The particular incubation conditions will vary depending on the specific nature of the analyte of interest and the specific binding pair member, where such conditions can be readily determined by those of skill in the art. For example, where the specific binding pair member is an antibody and the analyte of interest is an antigen, the incubation solution is generally buffered in the range of about pH 6.5–9.5. The incubation time should be sufficient for the targeted molecular bar code to bind available analyte molecules. Generally, from about 0.1 to 3 hr is sufficient, usually 1 hr sufficing. In an alternative example, where the analyte of interest is a particular DNA and the specific binding member is a DNA (or hybridizing mimetic thereof, e.g. PNA) having a sequence complementary to the sequence of the DNA of interest, conditions sufficient for hybridization are employed, where the conditions will generally be stringent conditions, for example, at 50° C. or higher and 0.1×SSC (15 mM sodium chloride/01.5 mM sodium citrate). Incubation results in the formation of specific binding complexes between the specific binding pair component of the targeted molecular bar code and the analyte(s) of interest, if present, in the sample being assayed.

Following complex formation, any unbound targeted molecular bar code is separated from the analyte/targeted molecular bar code complexes, i.e. the bound targeted molecular bar codes. Any convenient separation protocol may be employed, where the particular separation protocol that is chosen in a given assay will depend primarily on the nature of the analyte. Thus, where the analyte is large, e.g. a cell, one means of separation includes centrifugation, with cell bound targeted molecular bar codes being separated from unbound targeted molecular bar codes that are free in solution. Alternatively, where the analyte of interest, if present, is fixed to a solid support, e.g. a polynucleotide blot on nitrocellulose (such as a Northern blot), the substrate may be separated from the sample and washed to remove unbound targeted molecular bar codes. In yet other embodiments, the separation protocol may involve size separation protocols, with the analyte bound targeted molecular bar codes being separated from the unbound targeted molecular bar codes by methods that discriminate and separate based on size, such as chromatography, gel electrophoresis etc.

Following separation of the targeted molecular bar code/analyte complexes from the unbound or free targeted molecular bar codes, as well as any other sample constituents, the molecular bar code of the analyte/targeted molecular bar code complex is separated from the remainder of the complex, i.e. the specific binding pair member and the analyte. Separation generally is achieved through cleavage of the linker group. As such, separation typically involves treating the complex with an agent that cleaves the linking group. The agent that is chosen thus necessarily depends on the nature of the linking group. For example, where the linking group is a photocleaveable group, the agent may be light of appropriate wavelength to disrupt or cleave the photocleave-able group. In many embodiments, the wavelength of light used to cleave the photo-cleavable linking group ranges from about 180 nm to 400 nm, usually from about 250 nm to 400 nm and more usually from about 300 nm to 400 nm. Alternatively, where the agent is a chemically cleave-able group, the agent will be a chemical agent capable of cleaving the group, .e.g. dithiothreitol or beta-mercaptoethanol where the linking group is a disulfide. In yet other embodiments where the linking group is a restriction site, the agent is a catalytic agent, e.g. a restriction enzyme. Importantly, this cleavage step should not involve the use of agents which disrupt the nature of the molecular bar code, e.g. that hydrolyze it. This cleavage step results in the production of a cleavage product mixture comprising free molecular bar code and analyte/specific binding member complex.

Following the production of the cleavage product mixture, the free molecular bar codes present therein, if any, are detected and related to the presence of the analyte(s) of interest in the sample. Detection may or may not involve separation of the free molecular bar code from the remainder of the cleavage product mixture, as may be convenient or desired. The free molecular bar code is detected using any convenient protocol. Thus, in an embodiment where the bar code is capable of participating in Watson-Crick base pair interactions, the bar code may be detected with a complementary labeled nucleic acid, e.g. radioactive or fluorescently labeled RNA, where this detection step may or may not involve an amplification step, e.g. a PCR step.

Figure 4:
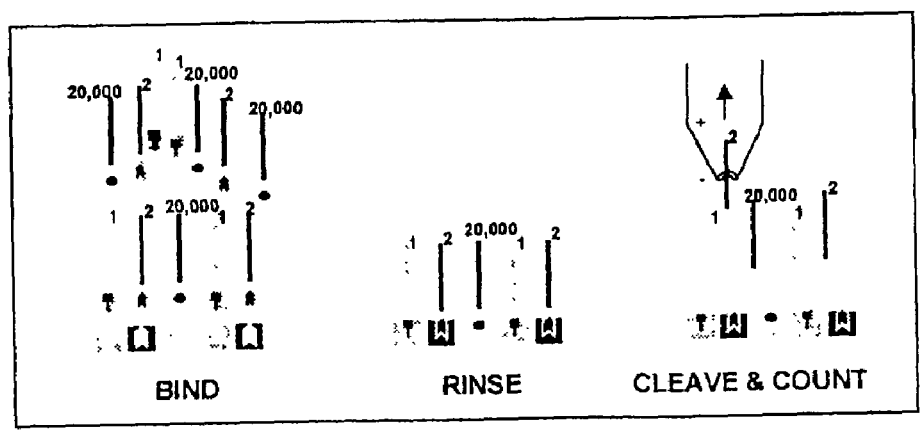
FIG. 4 provides a representation of a general approach using targeted molecular bar codes.
Figure 5:
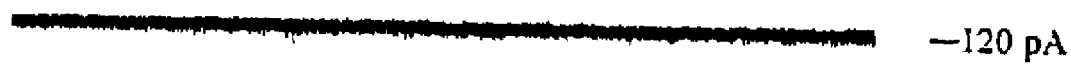
FIG. 5 shows the current fluctuations caused by a polydT (18) bar code. Comparison between unimpeded current in a nanopore and current fluctuations cause by a polydT(18) bar code. The tope tracing (A) shows unimpeded current through a single α-hemolysin channel at 120 mV in 1 M KCl. The lower tracing (B) shows blockades of the same channel current by polydT 18 mers at 20 µM concentration. At this concentration, the blockade frequency was about 50 per second. The duration of the blockades averaged about 50 microseconds.
Figure 5:
Figure 6:
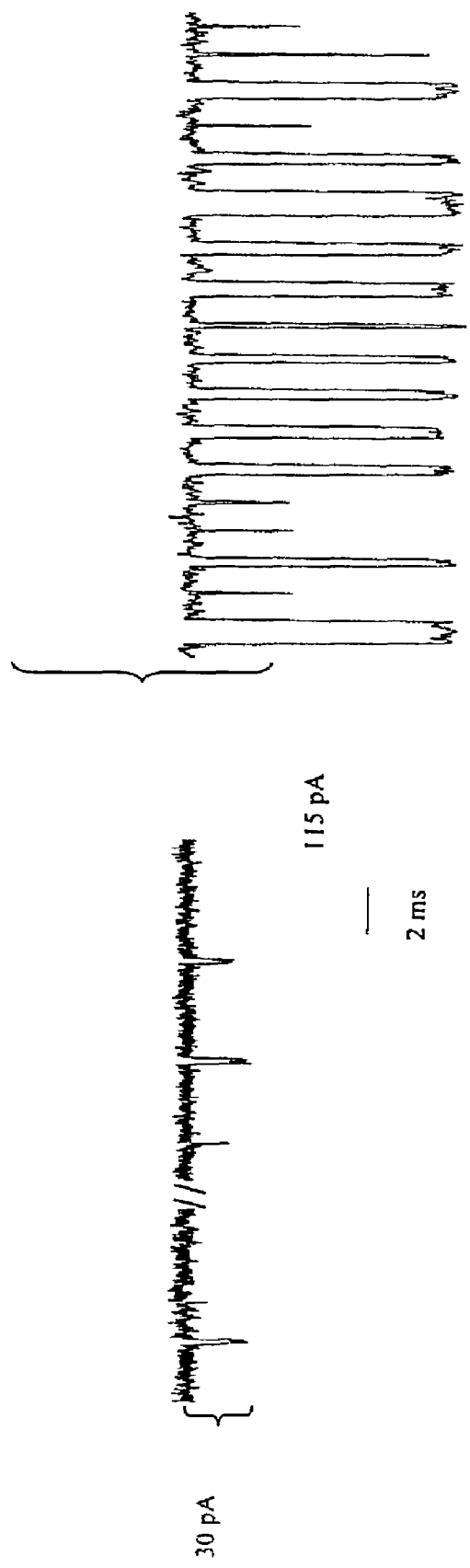
FIG. 6 shows the nanopore current blockades characteristic of a polyphosphate bar code and a polyC bar code. Nanopore current blockades characteristic of a polyphosphate bar code and a polyC bar code are shown. (A) Typical blockades caused by a nominal 65 mer of polyphosphate. The average amplitude of these blockades was 30 pA relative to the unimpeded channel current. (B) Typical blockades caused by a polycytidylic acid 125 mer. The average amplitude of these blockades was 115 pA. These two examples show the ca.85 pA range of blockade amplitudes that can be built into individual bar code blocks. This is sevenfold greater than the 12 pA difference that has been shown to be discernible within single RNA strands using a commercial patch clamp amplifier and the horizontal thin film device.

A particularly preferred means of detecting the molecular bar code is to translocate the molecular bar code through a nanopore under the influence of an applied electric field and observe the effect over time of the translocation on a measurable signal. One such measurable signal is blockade of ion current through a nanopore which generates a unique current blockade profile for each molecular bar code. In other words, the molecular bar code is "scanned" by translocating it through a nanopore, where the output of the scan is the current blockade profile. Once the current blockade profile is obtained, it can be compared to reference current blockade profiles to determine the exact identity of the specific binding member to which the molecular bar code was originally bound in the initial targeted molecular bar code. This comparing step and identification step can be done manually but is ideally performed by an appropriate computer hardware/software system. The above process is summarized in FIG. 4.

The nanopore device that is employed in the above preferred detection method is typically a device that comprises a nanopore inserted into a thin film with means for applying an electric field across the nanopore and for measuring the resultant signal at the nanopore. See FIG. 2. By nanopore is meant a structure having a channel or pore with a diameter of "nano" dimensions, where the inner diameter of the pore or channel typically ranges from about 1 to 10, usually from about 1 to 5 and more usually from about 1 to 2 nm. The nanopore may be synthetic or naturally occurring, where naturally occurring nanopores include oligomeric protein channels, such as porins, gramicidins, and synthetic peptides and the like, where a particularly preferred protein channel is the self-assembled heptameric channel of $\alpha$-hemolysin. In one embodiment, the thin film into which the nanopore is inserted is a lipid bilayer fabricated from a wide variety of one or more different lipids, where suitable lipids include: phosphatidlycholine, phosphatidylserine, phosphatidylethanolamine, glycerol monooleate, and cholesterol.

A variety of suitable thin film support devices have been reported in the literature that may be used to support the nanopore used to detect the molecular bar code. Such devices include those described in: Brutyan et al., Biochimica et Biophysica Acta (1995) 1236:339–344; Wonderlin et al., Biophys. J. (1990) 58:289–297; Suarez-Isla et al. Biochemistry (1983) 22:2319–2323 as well as those disclosed and reviewed in U.S. patent application Ser. No. 08/405,735 entitled "Characterization of Individual Polymer Molecules Based on Monomer-Interface Interactions" filed on Mar. 17, 1995 and having a University of California reference number of 91-287-2. Of particular interest is the device described in co-pending U.S. patent application No. 60/107,307 filed Nov. 6, 1998, the disclosure of which is herein incorporated by reference.

In detecting or "scanning" the molecular bar code with a nanopore device, the first step is to place the molecular bar code to be detected, e.g. the released or free molecular bar code generated from the cleavage step described above, on the cis side of the nanopore. The free molecular bar code will generally be in an aqueous solution, e.g. a buffered solution, where the solution typically comprises one or more dissolved salts, such as potassium chloride and the like, and the pH ranges from about 6.0 to 9.0, and more usually from about 7.0 to 8.5. The solution on the trans side of the nanopore may be the same or different from the solution on the cis side, but will also generally be an ionic buffered solution. After the free molecular bar code is placed on the cis side of the pore, an electric field is applied across the pore, conveniently by electrodes positioned in the cis and trans side of the pore. The electric field that is applied is sufficient to translocate the free molecular bar codes through the nanopore, and may range from about 50,000 to 500,000 volts per cm, where the applied electric field will typically range from about 100,000 to 400,000 volts per cm and more usually from about 150,000 to 300,000 volts per cm. During translocation of the molecular bar code through the nanopore, the ion current through the pore is measured. Measurements of individual molecular bar codes will typically be made at least every 1 s, usually at least every 0.1 s and more usually at least every 0.02 s using a single nanopore. The measured data values are then manipulated to produce a current blockade profile or similar output capable of being compared against reference outputs such that the identity of the molecular bar code can be determined. The presence of analyte (if any) in the sample is then related to the quantity of its specific molecular bar code detected that was detected by the bar code.

Because of the specific nature of the subject analyte detection assays employing the subject targeted molecular bar codes, amplification of the analyte or label associated therewith need not be performed prior to detection. Thus, the subject methods may be used to detect analyte in a sample at very low levels, where the amount may be as low as 20 picomole or lower but will at least be 1 zeptomole, and in certain embodiments at least 1 attomole. In addition, the presence of the analyte can be detected rapidly, usually in less than about 2 hours, and more usually in less than about 1 hour, where the time required for analyte detection may be as short as 1 minute or shorter, but will be at least 5 minutes in many embodiments.

The above analyte detection methods find use in a variety of different applications in which the detection of one or more analytes of interest is desired. Applications in which the subject methods find use include diagnostic and screening applications. Diagnostic applications include applications in which the detection of one or more specific analytes in a complex physiological mixture, such as the samples described above, is desired. In such applications, the presence of the analyte(s) of interest will generally be indicative of a particular disease or condition in the host from which the screened sample is derived. Thus, in diagnostic applications according to the subject invention, the presence of one or more analytes of interest is detected in a sample from the subject being diagnosed using the methods described above and then related to the presence or absence of a disease or condition.

In screening applications based on the subject methods, the subject targeted molecular bar codes are targeted, i.e. have a specific binding pair member that binds to an analyte of interest such as a toxin, bacterium, virion, pollutant and the like. As such, the screening applications can be used to screen physiological or environmental samples for the presence of man-made or naturally occurring toxins, pollutants, etc.

Also provided by the subject invention are kits comprising the subject targeted molecular bar codes. The number of different types of targeted bar codes in the kit may range widely depending on the intended use of the kit, where the number may range from 1 to 500,000 or higher, where any two targeted bar codes are considered to be of different type if their molecular bar code and specific binding pair member components are different. Thus, kits according to the subject invention may comprise a single type of targeted molecular bar code or 2 or more different types of targeted molecular bar codes, including sets of 4 different types of targeted molecular bar codes, sets of 10 different types of targeted molecular bar codes, sets of 64 different types of targeted molecular bar codes, sets of 100 different types of targeted molecular bar codes, sets of 1,000 different types of targeted molecular bar codes, sets of 100,000 different types of targeted molecular bar codes and sets of 500,000 types of targeted molecular bar codes. Thus, of interest are kits with at least 5, usually at least 10, more usually at least 15 different molecular bar codes, where the number of bar codes in these kits may be as high as 20, 100, 200, 500, 1000, 5000, 10,000, 20,0000 or more. In addition to the targeted molecular bar codes, the kits may further comprise one or more additional assay components, such as suitable buffer media, and the like. The kits may also include a device for detecting and scanning or reading the bar codes, such as those described supra, where the devices disclosed in copending U.S. patent application Ser. No. 60/107,307 filed on Nov. 6, 1998, are of particular interest. Finally, the kits may comprise instructions for using the targeted bar codes in methods of analyte detection according to the subject invention, where these instructions for use may be present on the kit packaging and/or on a package insert.

The following examples are offered by way of illustration and not by way of limitation.

EXPERIMENTAL

I. Preparation of a Horizontal Bilayer Containing a Single Nanopore Using a Miniature Horizontal Support A single channel was inserted into a bilayer on the horizontal aperture as follows:

A. Formation of diphytanoyl PC/hexadecane bilayers on a horizontal aperture.

A miniature support was manufactured as described under 'Preparation of Subject Devices' as disclosed in copending application Ser. No. 60/107,307 filed Nov. 8, 1998, the disclosure of which is herein incorporated by reference. A lipid bilayer was then formed as follows. The aperture and the Teflon bath holding the aperture were first cleaned for 10 min in boiling 5% nitric acid, then rinsed in nanopure water. Just before use, the aperture and bath were rinsed with ethanol followed by hexane, and then air dried. The aperture was then coated with a thin film of diphytanoyl PC (obtained from Avanti Polar Lipids, Birmingham, Ala.) by applying 5 µl of a 200 µg per mL solution in spectroscopy grade hexane which was then evaporated with a light stream of air injected through the U-tube from the trans side. The chambers on both sides of the aperture were then filled with 65 µl of buffer composed of 1.0 M KCl, 5 mM HEPES/KOH at pH 7.5. Silver chloride electrodes manufactured using standard methods were placed directly into each bath and were attached to an Axopatch 200B amplifier. To paint a bilayer, a single one-centimeter-long bristle on a 000 brush was dipped into a 3 mg per mL diphytanoyl PC solution in spectroscopy grade hexadecane. The bristle was then gently brushed across the aperture as viewed by a standard dissecting microscope. A 5 mV, 60 cycle square wave was applied across the aperture as a seal test. Once a seal was achieved the aperture was brushed repeatedly with a clean bristle until a capacitance of about 0.6 µF cm$^{-2}$ was achieved.

B. Insertion of individual α-hemolysin channels into the DiphytanoylPC/hexadecane bilayer.

α-hemolysin lyophilized in phosphate buffer (Calbiochem, La Jolla, Calif.) was dissolved in nanopure water at 2 µg per µl and dispensed as 2 µl aliquots into 0.2 mL polypropylene tubes. These aliquots were frozen at −20° C. On the day of an experiment, a single tube of toxin was placed on ice and diluted in 1.0 M KCl/HEPES buffer to a final concentration of 0.04 µg per µl. One µl of this diluted stock was added to the cis side of the bilayer and mixed gently. Voltage (120 mV trans positive) was then applied across the bilayer. A single channel typically inserted into the bilayer within 10–60 minutes as indicated by an abrupt increase in current. In the event that no channel insertion was observed in one hour, a second 0.04 µg aliquot of toxin was added. This generally resulted in a channel within an additional 15 minutes. Upon channel insertion, the cis chamber was immediately perfused with 2 mL of buffer, i.e. about 30 times the bath volume. Single rectifying channels (ca. 120 pA current in 1M KCl at 120 mV potential trans positive) were used immediately for molecular bar code analysis.

II. Use of the Device

The nanopore device described above was used to characterize molecular bar codes as follows:

A. Preparation of Molecular Bar Codes

1. Preparation of RNA Homopolymer Molecular Bar Codes

Homopolymers of polycytidylic acid and polyadenylic acid (2000+nt) were purchased from Fluka (Ronkonkoma, N.Y.). To generate shorter fragments, 5 mg of full length RNA homopolymers were weighed into a 12 mL polypropylene tube. To this was added 1 mL of alkaline buffer (pH 10.2, 40 mM NaHCO$_3$, 60 mM Na$_2$CO$_3$) pre-warmed to 60° C. For a product ranging in size from 100 to 500 nt in length, the solution was incubated at 60° C. for 23.5 minutes and the reaction stopped by adding 100 µl of 3 M sodium acetate, pH 5.2, and 50 µl of 10% glacial acetic acid. The RNA was precipitated in 2.5 volumes of ethanol at −20° C. The pellet was rinsed in 80% ethanol, then redissolved in 1 volume water and 1 volume 2× formamide loading buffer (90% formamide, 10% 10×MOPS RNA buffer). The product was loaded on an 8% polyacrylamide/MOPS gel and run at 4 volts per cm alongside RNA markers (Century Markers, Ambion Inc., Austin, Tex.). The gel was then examined by UV shadowing and RNA fragments of varying length were excised and eluted from the gel by electrophoresis. The sized RNA was then ethanol-precipitated and redissolved in water or pH 7.5 TE buffer at 2-to-5 µg per µl.

2. Synthesis of a Molecular Bar Code Comprised of an RNA Block Copolymer

A 134 base DNA oligo-nucleotide composed of the sequence (SEQ ID NO:01)
TAATACGACTCACTATAGGGA(A$_{29}$)/C($_{70}$)GGTACCACACAC was purchased from Midland Certified Reagents (Midland, Tex.). Full-length 134 nt strands were separated from incomplete strands by electrophoresis on an 8% preparative PAGE/TBE gel at 100 V for 4 hours. The desired band was excised, the full length material was electroeluted from the gel slice, precipitated in ethanol, rinsed twice with 80% ethanol, air-dried, then dissolved in water to give a final concentration of 1 µg per µl.

Double-stranded template was synthesized from the purified single-stranded 134mer using Sequenase (Amersham/U.S. Biochemical, Cleveland, Ohio). Briefly, 1 µg of the 134mer (25 pmol final) were combined with 0.2 µg of a 14 base reverse complement to the 3' end of the 134 mer (50 pmol final), 4 µl of Sequenase 5× buffer, and 3 µl nanopure water. This mixture was heated to 65° C. for 2 minutes and gradually cooled to 4° over 30 minutes to permit annealing of the reverse complement to the 134 nt strand. This solution was then heated to 37° for two minutes and combined with 1 µl 0.1 M DTT, 2.4 µl of a 2.5 mM dNTP mixture at room temperature, and 6 µl of pure water. This solution was brought to 37° C. for 1 minute, combined with 1 µl of 13U per µl Sequenase and then incubated at 37° C. for 45 minutes. The resulting double-stranded DNA product was stored at −20° C.

RNA was synthesized using the 134 nt double-stranded DNA template and a T7 RNA polymerase-based kit designed to give very high yields of short transcripts (Megashortscript, Ambion Inc., Austin, Tex.). Briefly, we combined, in order, at room temperature, 4 µl nanopure water, 2 µl 10× transcription buffer, 2 µl each of 75 mM ATP, CTP, UTP, GTP, 4 µl of dsDNA template from the previous step, and 2 µl Megashortscript(T7 RNA polymerase) enzyme stock. This mixture was incubated at 37° C. for 2 hours. At the end of the incubation, 1 µl of 2U/µl DNAse 1 was added along with 0.25 µg of RNAse T1(Life Technologies) to cleave undesired ends of the RNA product at G residues. This digestion was incubated at 37° for 15 minutes. The product was then run on an 8% PAGE gel in 1×MOPS RNA buffer at 80 V. The desired 101 nt band was excised and eluted by electrophoresis. The elution buffer was then exchanged for pH 7.5 TE buffer using a Bio-Rad 30 spin column (Hercules, Calif.). The final product was stored at 2 µg per µl in a −20° C. freezer.

3. Synthesis of Molecular Bar Codes Using a DNA Synthesizer

Molecular bar codes were synthesized by conventional phosphoramidite chemistry using an automated device. The coupling and deprotection steps were in accordance with standard methods recommended by the manufacturer of the DNA synthesizer. The synthesis scale ranged from 40 nmol to 1 µmol, and the column support was typically dT-CPG with a pore size of 500 angstroms to 1000 angstroms. These syntheses were typically performed 'trityl on' after the last coupling step, permitting purification of full length molecular bar codes using a widely practiced column chromatography procedure. An example molecular bar code synthesized using 69 coupling reactions at 0.2 umol scale was:

$$PolydT_{(33)}/PEG_{(18)}/dT_{(1)}/PEG_{(18)}/polydT_{(34)}$$

Figure 8:
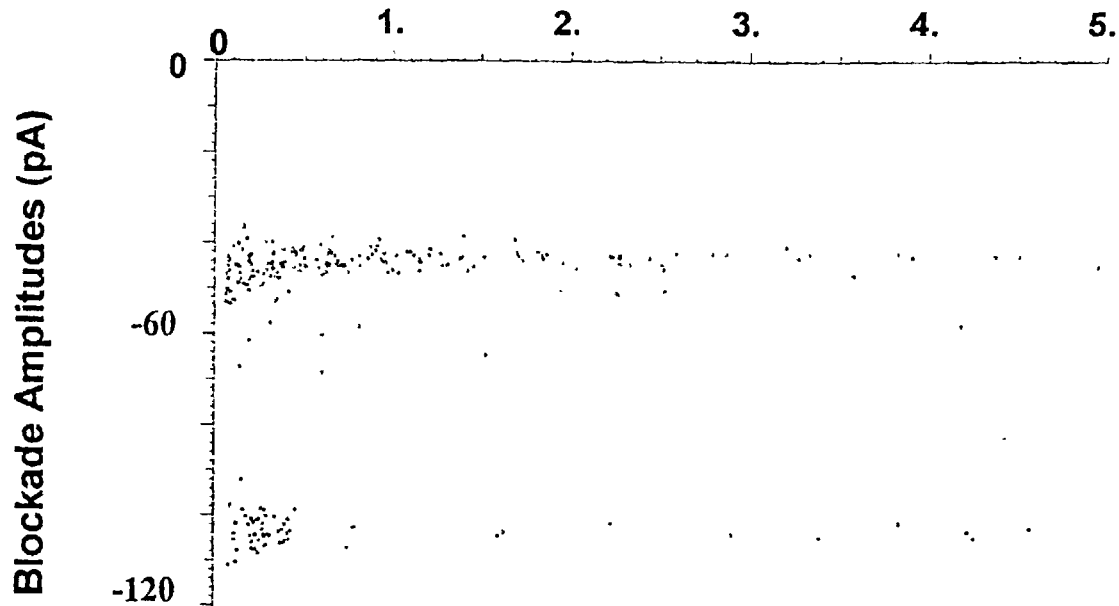
FIG. 8. Current profile analysis for a bar code comprised of polydT oligomers linked to polyethylene glycol (C18) spacers. Specifically, this figure shows the event pattern caused by a block copolymer comprised of polydT DNA oligomers linked via phosphodiester bonds to non-DNA polyethylene glycol (C 18) spacers. This molecular bar code (polydT$_{(33)}$/PEG18/dT$_{(1)}$/PEG18/polydT$_{(34)}$) was synthesized on an ABI 392 synthesizer using conventional phosphoramidite chemistry.

A current blockade profile for this molecular bar code is illustrated in FIG. 8.

In one embodiment, an automated DNA synthesizer is used to directly couple a bar code to a DNA oligomer that is a reverse complement to a targeted gene (e.g. *Xenopus* elongation factor). A cleave-able site (the Xba I recognition sequence) is built into the synthetic strand between the bar code and the specific binding pair member using a hairpin and a C18 spacer. The complete targeted molecular bar code is then 5nitroindole(20)/Spacer9/dT(1)/Spacer9/
dT(17)TCTAGAGCGCTTTGCGCTCTAGA/

Spacer 18/GTGTCCAATGACAACGATGTTGATGTGAGTCTTTTCCTTT (SEQ ID NO:02)

This molecule is applied to a membrane blot that is thought to contain Xef mRNA. Following equilibration, unbound targeted molecular bar code is washed from the surface. The bound material is then digested with Xba I which cuts the strand at the Xba I recognition sequence in the hairpin stem, thus releasing the 5nitroindole(20)/Spacer9/dT(1)/Spacer9/dT(17) molecular bar code for analysis using a nanopore.

B. Current Blockades Produced by Molecular Bar Codes

1. Single Channel Current Recordings.

Current readings across single α-hemolysin channels were acquired using an Axopatch 200B integrating patch clamp amplifier (Axon Instruments, Foster City, Calif.) in voltage clamp mode. Unless otherwise noted, data were acquired at 10 µs intervals in the whole cell configuration and were filtered at 10 kHz using a low-pass bessel filter. The analog signal was digitized using an Axon Instruments Digidata 1200 Series Interface, and then stored using pClamp 6.02 software (Axon Instruments, Foster City, Calif.). Before the addition of molecular bar codes to the cis chamber, data were acquired in gap free format for 15 seconds each at 0, +120m V, and −120 mV. Molecular bar codes (10–15 µg unless otherwise noted) were added to the cis chamber, and blockades of current were examined at 120 mV (trans positive) for five minutes. Blockades were stored in pClamp 6.02 using the event driven format.

2. Quantitative Discrimination between RNA Molecular Bar Codes Using a Nanopore

Figure 7A:
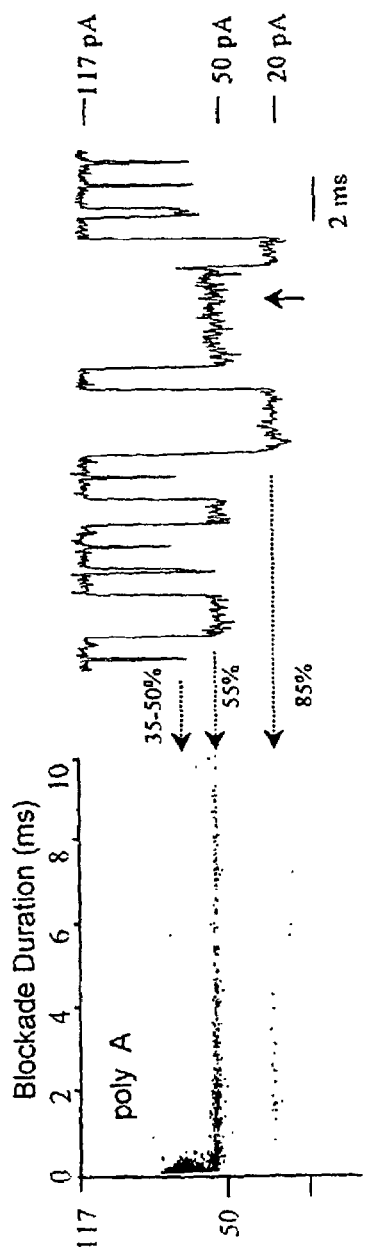
FIG. 7. Current profile analysis demonstrating that a nanopore device can discriminate between different bar codes in a mixture. (a) is polyA; (b) is polyC and (c) is polyA+polyC.
Figure 7B:
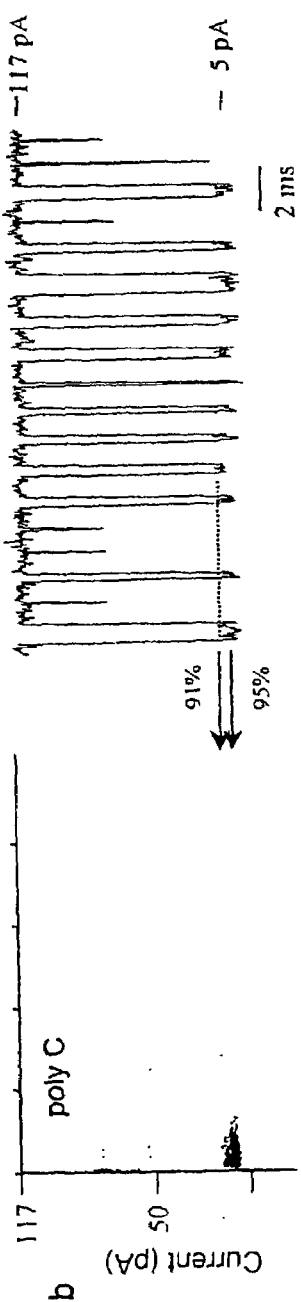
Figure 7C:
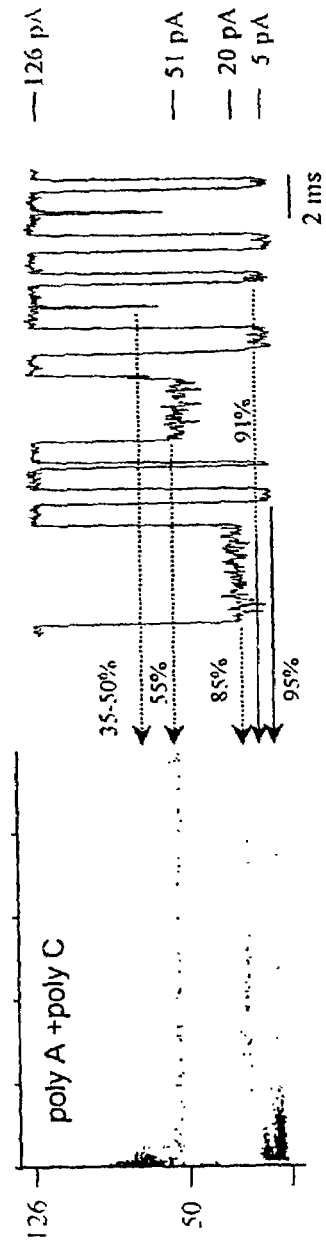

Blockades of ionic current caused by occupancy of the α-hemolysin pore by the polyadenylic acid (polyA RNA) bar code were measured first. The polyA blockades (FIG. 7a) fell into three populations: i) relatively short (<200 µs) blockades that reduced the current by 40–60 pA; ii) blockades of indeterminate length that reduced the channel current by 65 pA to a residual current of about 50 pA (55% blockades); and iii) blockades of 1.5 to 2.5 ms that reduced the channel current by about 98 pA to 19 pA of residual current (84% blockades). The duration of the third class of blockades was strand-length dependent, whereas the duration of the first two classes was length independent (data not shown). The pattern of blockades caused by polyC bar codes was easily distinguishable from the pattern for polyA bar codes whether the polymers were examined separately (FIGS. 7a and 7b) or in combination (FIG. 7c). That is, the channel current was reduced significantly more by the polyC RNA bar code (typically 95% blockades) than by the polyA RNA bar code (84% blockades) and the polyC blockades were shorter in duration, averaging 6 µs per nucleotide compared to 16 µs per nucleotide for polyA. Also, polyC RNA rarely induced lower amplitude blockades or biphasic blockades that were very common with polyA RNA. This constitutes proof of principle that the nanopore can quantitatively discriminate between a mixture of molecular bar codes in an aqueous solution.

3. Detection of Blocks within Individual RNA Molecular Bar Codes

Figure 3:
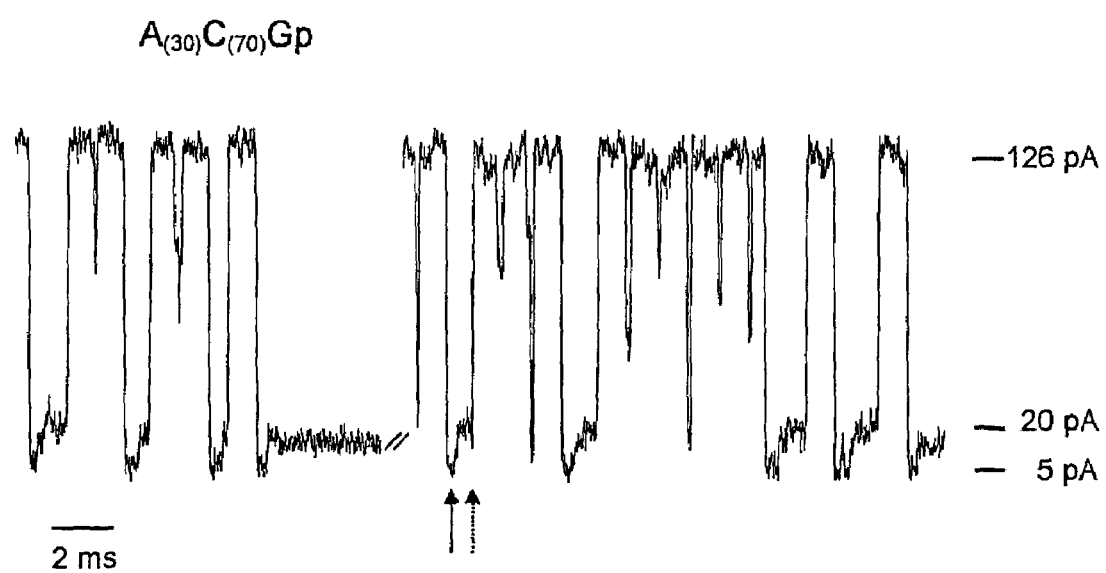
FIG. 3 provides an example of a current blockade profile caused by a molecular bar code. Specifically, FIG. 3 provides an example of a current blockade profile caused by a molecular bar code. A single α-hemolysin channel was inserted into a bilayer giving an open current of 126 pA at 120 mV in 1 M KCl buffer. During control measurements in the absence of a bar code, virtually no blockades were observed. Addition of $A_{(30)}C_{(70)}$Gp bar code to the cis bath immediately produced blockade events at a rate of approximately 1 per second. In this experiment, most bilevel events first exhibited 5 pA residual current (95 percent current blockade, solid arrow) followed by a 19 pA residual current (84 percent blockade, dashed arrow).

The preceding experiment suggested that a transition from polyA to polyC blocks within individual bar codes should be detectable by the α-hemolysin pore. To test this prediction, in vitro transcription and ribonuclease T1 digestion was used to generate a 101-nucleotide-long RNA bar code of the nominal composition A(30)C(70)Gp (section IIA.2 above). Typical biphasic blockades caused by occupancy of the channel by this bar code are shown in FIG. 3. As predicted, one component of the blockade reduced the channel current by 95% (consistent with the polyC block of the bar code), and the other component reduced the current by 84% (consistent with the polyA block of the bar code). This proves the principle that blocks can be read along single molecular bar codes using a nanopore.

4. Establishment of a Unique Current Blockade Profile for a Molecular Bar Code Comprised of DNA and Non-DNA Blocks A molecular bar code of the composition:

$$polydT_{(33)}/PEG_{(18)}/dT_{(1)}/PEG_{(18)}/polydT_{(34)}$$

was synthesized on an ABI Automated DNA synthesizer using conventional phosphoramidite chemistry as outlined in Section II.A.3 above. This molecule was then examined using a nanopore as described in Section II.B.1, revealing a unique current blockade profile (FIG. 8) that was readily distinguishable from the other molecular bar codes listed in this application III. Detection of N-ras in a Complex Sample A. Synthesis of an N-ras Targeted Molecular Bar Code and its Use for Specifically Detecting a Segment of N-ras Exon 1.

Figure 9:
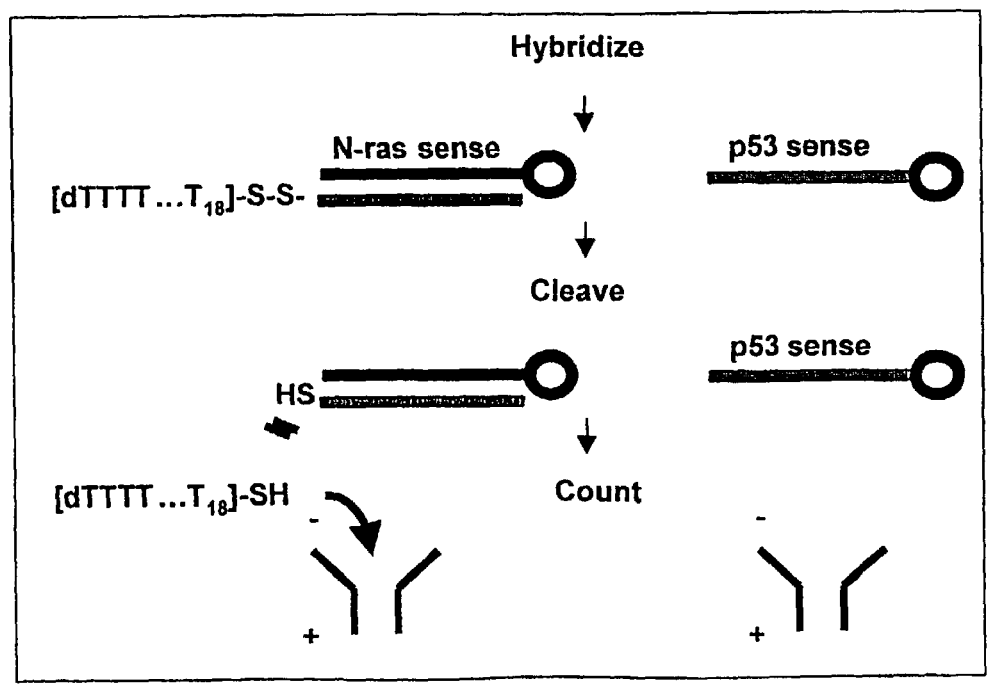
FIG. 9 provides a schematic diagram of the protocol used to detect N-ras, as described in the Experimental Section, Infra.

A targeted molecular bar code was synthesized at 1 µmol scale on an ABI 392 DNA Synthesizer using standard conditions. The targeted bar code (top of FIG. 9) was composed of a poly $dT_{18}$mer at its 5' end, linked by a disulfide bond (Glen Research, Sterling, Va.) to a 50 base-long, anti-sense segment of N-ras Exon 1. This targeted bar code (10 µM final concentration) was hybridized at 40 degrees C. for four hours in 6×SSC to either a 40 base segment of N-ras Exon 1(sense strand) or to a 70 base segment of the p53 open reading frame. Each of the target oligonucleotides was attached to polystyrene beds to facilitate recovery and washing of the bound bar code. Following hybridization, the beads were washed twice in 0.2×SSC at room temperature. The beads were then suspended in 20 µl of 0.1 M DTT (pH 8.3/Tris) for 30 minutes to cleave the disulfide linkage between the $dT_{18}$ code and the N-ras targeting sequence. The beads were subsequently spun down and the $dT_{18}$ bar code was recovered in the supernatant. One half the supernatant was then added to ca. 100 µl of 1M KCl buffer bathing a single alpha hemolysin nanopore. The recovered bar codes were then counted by translocating them through the pore at 150 mV applied potential and identifying $dT_{18}$-specific channel blockades. A diagram of the above protocol is provided in FIG. 9.

B. N-ras Specific Bar Codes Detected by the Alpha Hemolysin Nanopore.

Figure 10:
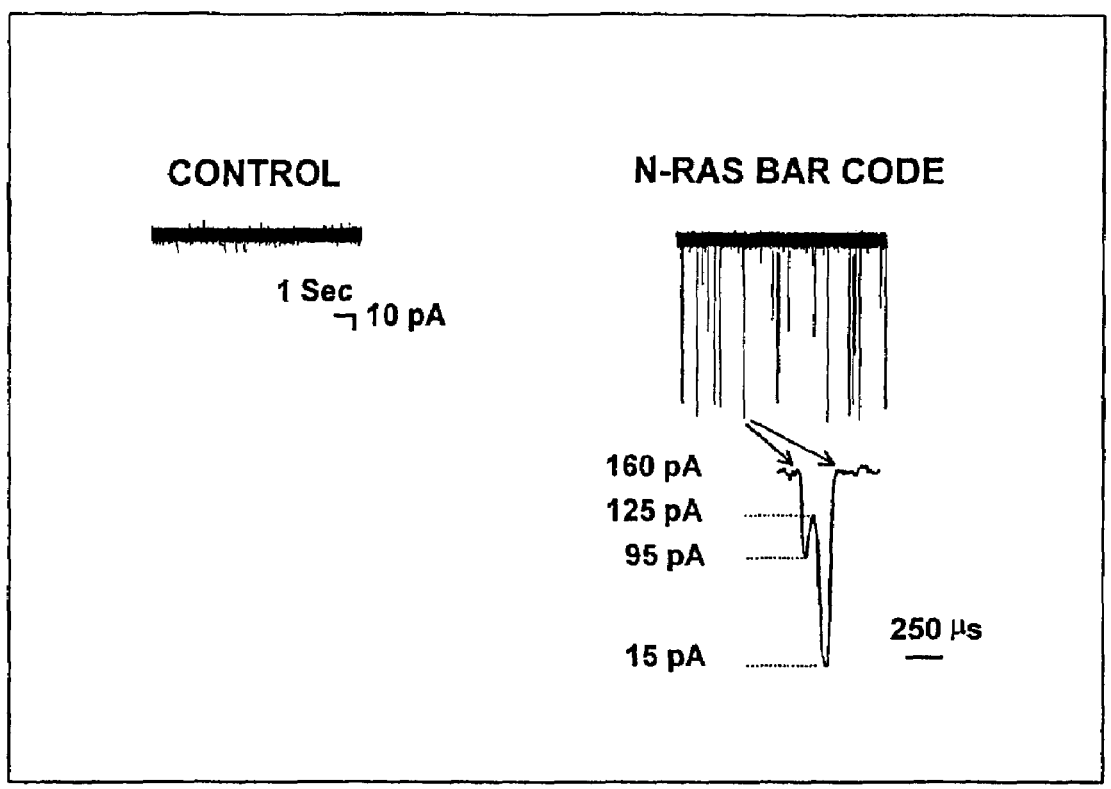
FIG. 10. Current profile analysis of N-ras bar code.

FIG. 10 provides the results following detection of the bar codes obtained from A above. Panel A of FIG. 10 shows the unimpeded current through a single alpha hemolysin channel at 150 mV in 1M KCl (HEPES/pH 8.0). Panel B shows the current through the same channel following addition of bar codes that had been cleaved from the N-ras antisense strand hybridized to N-ras target beads. Panel C depicts an expanded view of a blockade pattern specific to the $dT_{18}$ code cleaved from the N-ras targeting sequence. Only blockade events with this specific pattern were counted as positive results. These results are presented in the following Table 1.

TABLE 1

Quantitative measure of N-ras targeted bar codes hybridized to a gene specific target and to a negative control.

| Bar Code Targeting Sequence | Target Sequence | N-ras Specific Bar Code Signatures (Counts per Assay ± S.E.) |
|---|---|---|
| N-ras α-sense 50mer | N-ras sense oligo Attached to polystyrene bead | 50 + 14 |

TABLE 1-continued

Quantitative measure of N-ras targeted bar codes hybridized to a gene specific target and to a negative control.

| Bar Code Targeting Sequence | Target Sequence | N-ras Specific Bar Code Signatures (Counts per Assay ± S.E.) |
|---|---|---|
| N-ras α-sense 50mer | p53 sense oligo Attached to polystyrene bead | <1 |

The above results demonstrate that a molecular bar code can be specifically targeted to a macromolecule of interest, then cleaved from the targeting moiety at a linker, and finally quantified using a nanopore detector.

IV. Synthesis of Molecular Bar Codes with Hairpin Structures

A. Bar Code Synthesis.

DNA oligonucleotide bar codes were synthesized by conventional phosphoramidite chemistry using an ABI 392 DNA Synthesizer. Each molecule was composed of 20 dC monomers at the 5' end, followed by a hairpin with a 4 dT turn and a 0–10 bp stem, and then by 20 additional dC monomers at the 3' end. As controls, oligonucleotides with the identical chemical compositions but scrambled sequences were also synthesized. These oligonucleotides were purified by PAGE and stored in TE buffer at −20 degrees centigrade.

B. Characterization

Figure 11A:
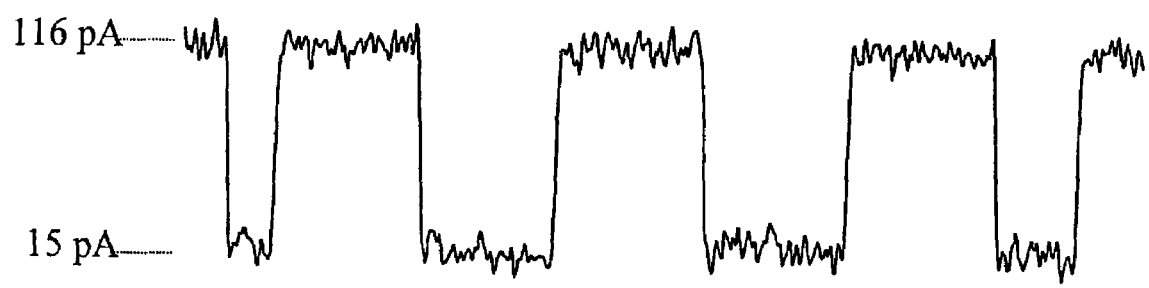
FIG. 11. Comparison of blockade durations for a) polydC oligomer with an internal 10 bp hairpin and b) a polydC oligomer with the same nucleotide composition but in random order.
Figure 11B:

The effect of hairpin structure on oligonucleotide transport through a model nanopore was tested by adding purified preparations to a 70 µl bath containing 1 M KCl buffered at pH 8.0 (HEPES/KOH) and at room temperature. 80 to 200 mV potential was applied across a diphytanoyl phosphatidylcholine bilayer containing a single α-hemolysin nanopore. This applied voltage permits capture and translocation of the anionic DNA strands by the nanopore which can be read as an abrupt decrease in monovalent ion current. The duration of the current blockade is an accurate measure of the time required for an individual strand to translocate across the nanopore. Typical blockades are shown in FIG. 11.

Figure 12:
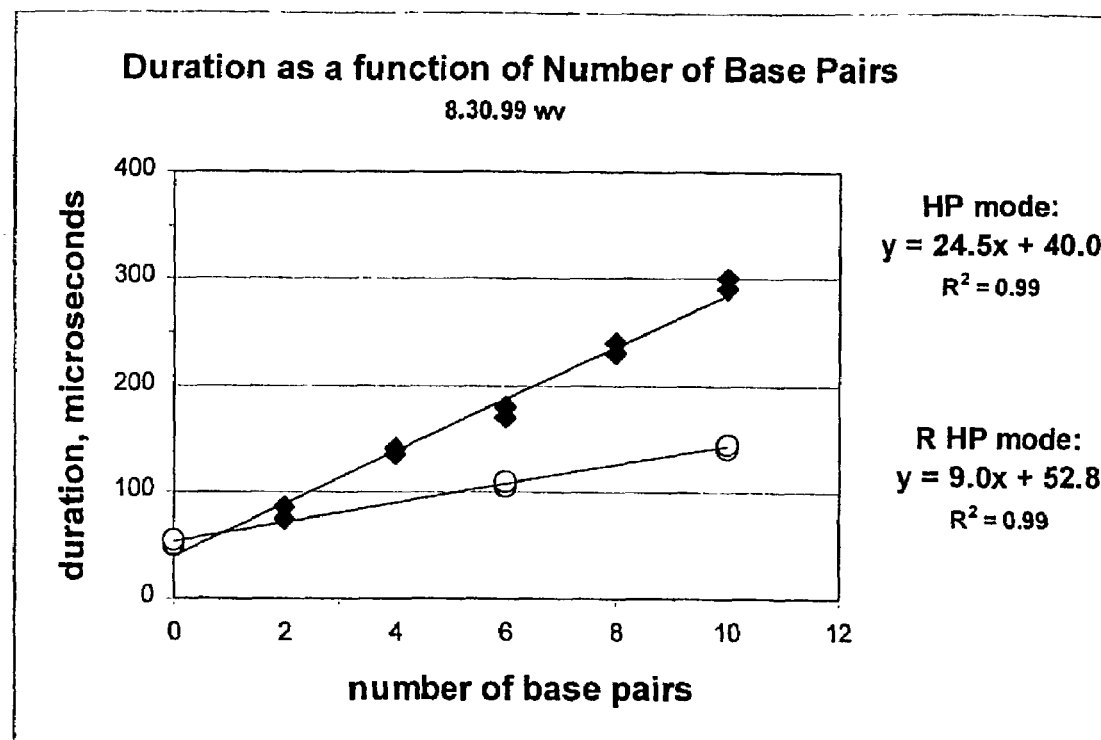
FIG. 12. Blockade duration as a function of number of base pairs in hairpins inserted into polydC oligomers. The upper line (dark diamonds) represents the duration mode for oligomers with base-paired hairpins. The lower line (open circles) represents the duration mode for oligomers with the same nucleotide composition but randomized.
Figure 13:
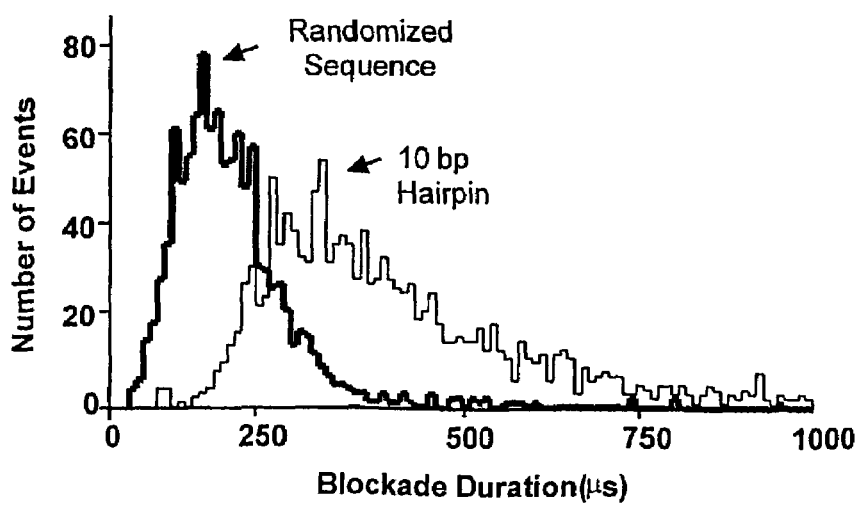
FIG. 13. Discrimination between polydC oligomers with 10 base-pair hairpins and oligomers with randomized sequence based on blockade duration. Each population includes approximately 1000 blockade events.

FIG. 12 shows that including hairpins with 2-to-10 base pair stems in DNA oligomers increases the blockade duration by 15–18 µs per base pair relative to randomized controls. A two-base pair difference is easily distinguishable. Furthermore, oligomers containing different number of base pairs but the same number of monomer units can be distinguished based on blockade duration alone given a sample size of one zeptomole (1000 molecules) (FIG. 13). Thus, introduction of a hairpin into a synthetic DNA strand provides an unambiguous means to distinguish between two 'bar code' populations at high sensitivity based on residence time in the nanopore.

Figure 14:
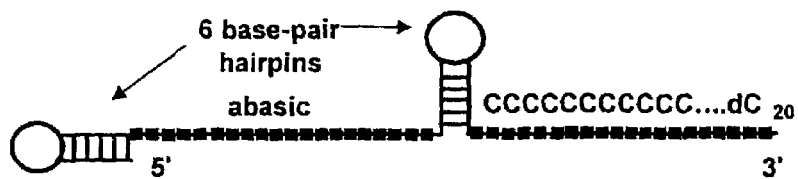
FIG. 14. A model molecular bar code containing two 6 base-pair hairpins designed to control the rate of translocation through the nanopore.
Figure 15:
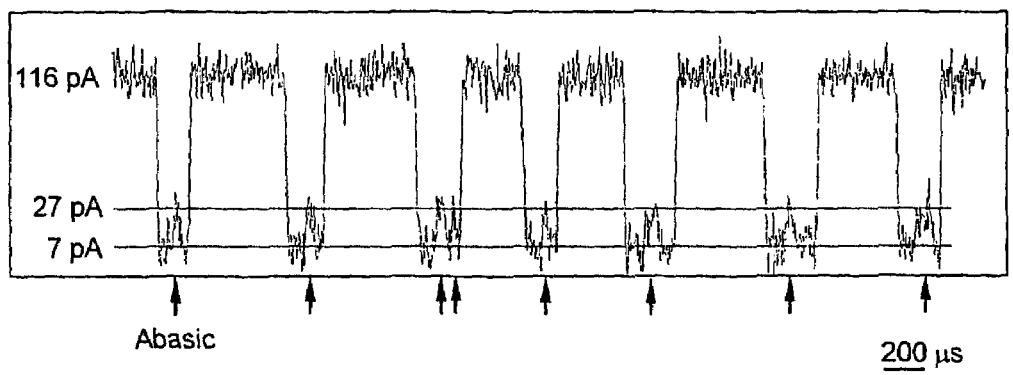
FIG. 15. Current blockades caused by the oligonucleotide diagrammed in FIG. 14. The arrows indicate an abrupt current increase that correlates with occupancy of the pore by an abasic segment built between poly dC segments.

The base pairing structure also acts as a built-in pause to provide a better signal-to-noise ratio for distinct portions of an encoded polymer. For example, a section of abasic units in a molecular bar code passing through a nanopore should give a transient increase in current because the smaller size of the units will block the current less. But, the speed at which these highly charged units pass through the channel makes them unobservable. To pause the molecular bar code and make the observation possible, a 6 base-pair stem was inserted into an oligonucleotide before and after a 20 monomer-long abasic segment (FIG. 14). This resulted in an easily observable current transition during occupancy of the pore by the abasic segment of the encoded polymer (FIG. 15). Specifically, when this molecule was translocated through the α-hemolysin nanopore under a 120 mV applied potential, a three part blockade signature was clearly evident in which the first blockade component was characteristic of poly dC (14 pA or 89% current reduction relative to the open channel), the second component was characteristic of a deoxyribose-phosphate polymer (43 pA or a 66% current reduction) and the last component was characteristic of random DNA sequence (13 pA or a 90% current reduction) (FIG. 1b). This experiment demonstrates that a synthetic polymer can be read by a nanopore, and that multiple component signals are detectable.

The above results demonstrate that inclusion of hairpin loop structures into molecular bar codes modulates the characteristics of the bar codes. These built-in secondary structures allow better control over the rate of polymer translocation through the nanopore. That is, encoded polymers made from extended, single-stranded DNA traverse the α-hemolysin nanopore at a rate of 1–3 μs/nucleotide. The above demonstrates that including hairpin structures with 2-to-10 base pair long stems increases the traversal time by 15–18 μs per base pair. This temporal control is important for two reasons: 1) slowing traversal permits a longer read time for each coding segment in the pore, which results in a much better signal to noise ratio and higher fidelity; and 2) building hairpins into the polymers allows one to use the traversal time as part of the code. For example, we have shown that oligomers containing different numbers of base pairs but the same number of nucleotides can be distinguished from one-another with a sample size of 1000 molecules (one zeptomole). The above described secondary structures may be incorporated into any type of bar code to provide for modulated properties, where such bar codes also include those described in V supra, e.g. e.g. polyacrylic acid or polystyrene containing bar codes. In addition, non-DNA secondary structures could be built into the bar codes and to regulate translocation in like manner.

Figure 16:
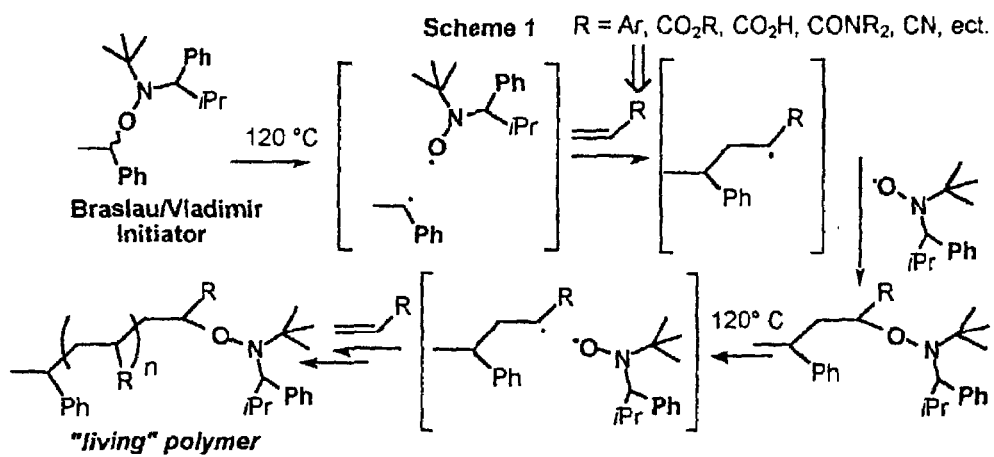
FIG. 16. Schematic of living polymerization reaction using Braslau/Vladimir initiator.

V. Preparation of Synthetic Polymers for Use in Molecular Bar Codes via Nitroxide-Mediated Radical Polymerization Nitroxide-mediated radical polymerizations were used to prepare synthetic polymers, where the protocols employed are based on the 'Braslau/Vladimir Initiator.' See the relevant literature section, supra. This technique is used to effect "living" polymerizations with extremely low polydispersities and controlled molecular weights for a number of monomer families, including styrenes, acrylates, acrylic acids, and acrylonitriles (FIG. 16). Using the Braslau/Vladimir initiator, controlled polymers (including block copolymers) bearing a variety of functionalities, including carboxylic acids, epoxides, amines, perfluoroalkyl groups, ethers, esters, amides, nitriles and substituted aromatic groups, are prepared. In addition, polymers with more complex topologies, such as comb, star and dendritic structures are prepared. As such, this method enables the production of a large number of unique bar codes that can be utilized in targeted molecular bar code structures. In other words, these preparation methods permit synthesis of molecular bar codes with a large selection of interchangeable polymer blocks. Furthermore, molecular bar codes with backbones inert in biological media can be synthesized.

Figure 17:
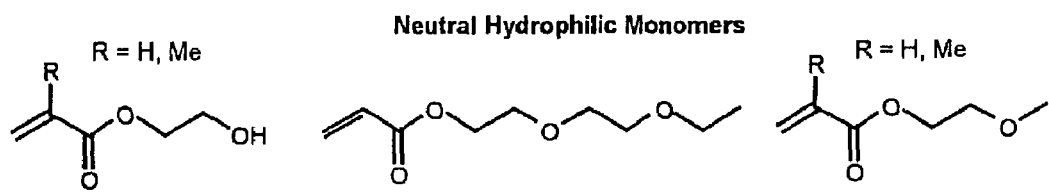
FIG. 17. Representative hydrophilic monomers that may be used in the molecular bar codes.
Figure 18:
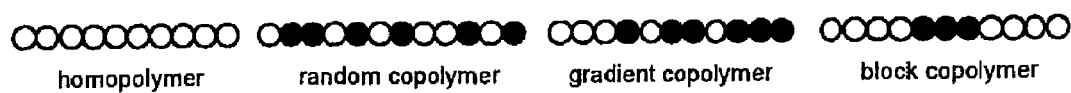
FIG. 18. Representative motifs in copolymers of the subject invention.
Figure 19:
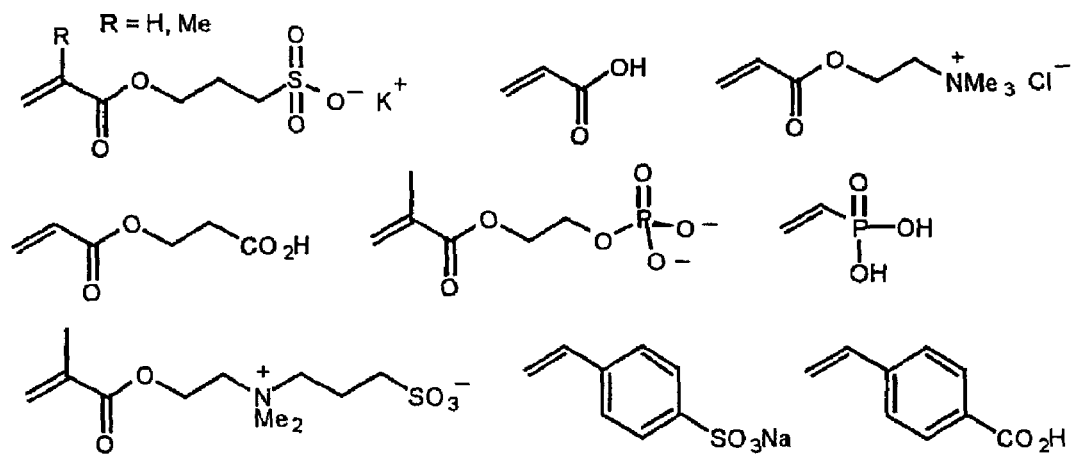
FIG. 19. Charged or ionizable monomers that may be employed in the subject molecular bar codes.

A representative protocol is as follows. Polymer bar codes are prepared using nitroxide-mediated living free radical polymerization with an alphabet of commercially available monomers. Both acrylates and styrenes have been shown to function well using the Braslau/Vladimir initiator. Initial bar codes are designed using these monomer classes as substrates. Water solubility is designed into the polymers by the use of hydrophilic acrylate or methacrylate derivatives to form neutral hydrophilic backbones (FIG. 17). Charged monomers are mixed into these backbones as either bulk random copolymers, gradient copolymers (achieved by syringe pump addition) or block copolymers (FIG. 18). A few examples of each monomer class are shown here, all of which are commercially available (FIG. 19).

Polymerizations are typically carried out at 120° C. with 0.05 equivalents of the Braslau/Vladimir initiator and 50 to 200 equivalents of monomer. We have previously demonstrated random copolymerization using n-butyl acrylate and a variety of functionalized acrylate monomers (200 equivalents): good polydispersities (<1.2) are typically obtained with ratios of up to 80/20 t-butyl acrylate/copolymer. Vinyl phosphonates are also of interest. Block copolymers starting with acrylates followed by styrene have given good results using our initiator. Acrylate/acrylate block copolymers are of interest as well.

Figure 20:
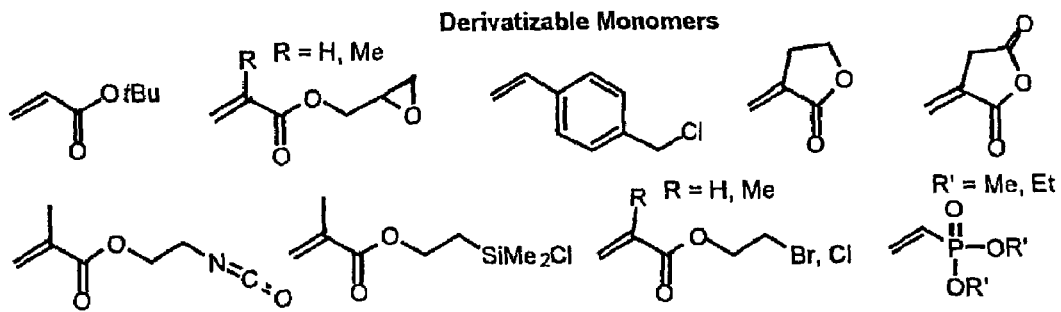
FIG. 20. Derivitizable monomers that may be employed in the subject molecular bar codes.
Figure 21:
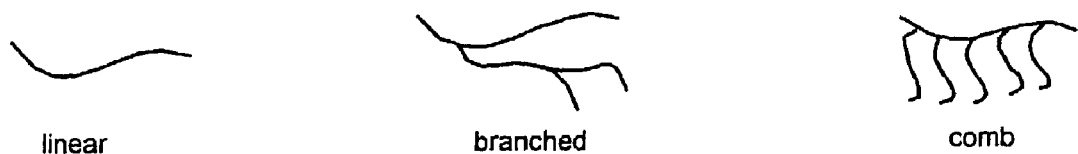
FIG. 21. Motifs of different branched polymers that may be employed in the subject bar codes.

Derivatizable monomers can also be introduced into the polymer bar codes (FIG. 20). These can be protected forms of ionizable species. For example, t-butyl acrylate can be used as a protected form of acrylic acid: treatment of the used as a protected form of acrylic acid: treatment of the polymer with TFA should liberate the carboxylic acids. Vinyl phosphonate esters can serve as a protected form of phosphonic acids. Alternatively, these derivatizable monomers can be used as handles for the introduction of additional charged or fluorescent moieties; these can be added after the polymerization has been effected. In addition, the use of monomers with reactive functionality offers the opportunity to introduce graphed arms onto the polymer chain. This can be used to manipulate the effective diameter of the polymer chain, or to design more complex structures such as branched or comb polymers (FIG. 21). The introduction of lipophilic and/or sterically bulky residues into the bar codes (pre or post-polymerization) provides further modulation of the bar code profile.

Figure 22:
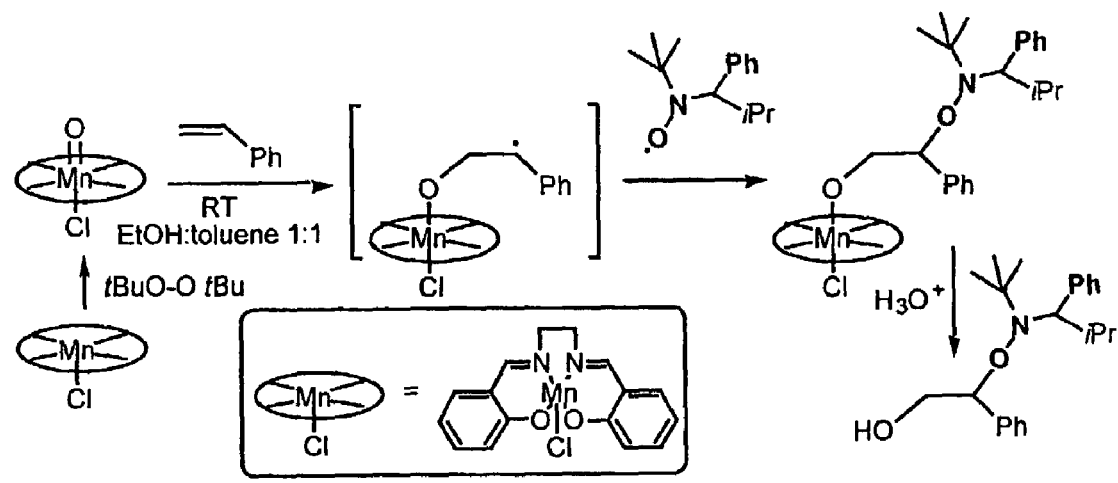
FIG. 22. Schematic for preparation of functionalized nitroxide Braslau/Vladimir initiator.
Figure 23:
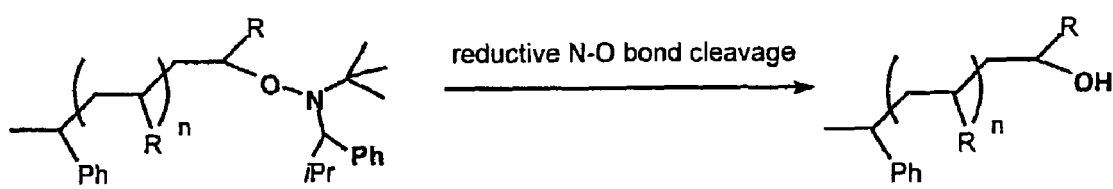
FIG. 23. Schematic for preparation of secondary hydroxy group at the terminus of a bar code.

After polymerization, the bar codes can be designed to be attached to the targeting peptides at either the beginning or terminal end. Hawker's route (FIG. 22) can be used to prepare an initiator with a pendant primary hydroxy group, or reductive cleavage of the "living end" of the polymer with Zn/HOAc, Na/Napth or SmI$_2$ can be used to leave a secondary hydroxy group on the bar code terminus (FIG. 23).

The above results demonstrate that a large number of diverse polymers that can be used as targeted molecular bar codes may be synthesized using nitroxide mediated polymerization protocols.

VI. Preparation of Labile Linkers

Photolabile Linker:

Photolabile linkers based on vanillin are synthesized as follows. Treatment of vanillin 1 with K$_2$CO$_3$, provides alkylation of the phenol with 6-Bromohexanoic acid, yielding 2. 2 is then nitrated with fuming HNO$_3$ and acetic acid to yield 3. 3 may be protected at the carboxylic acid with TMS depending on the stability of the final product. This step may or may not be necessary. 4 will be reduced to 5 with NaBH$_4$. At which point 5 will be phosphitilated to the corresponding phosphoramidite 6. 6 Can be used in a synthesizer to couple the linker to an oligo, or in solution phase coupling. Below, a proposed synthesis is presented in scheme 1.

Scheme 1

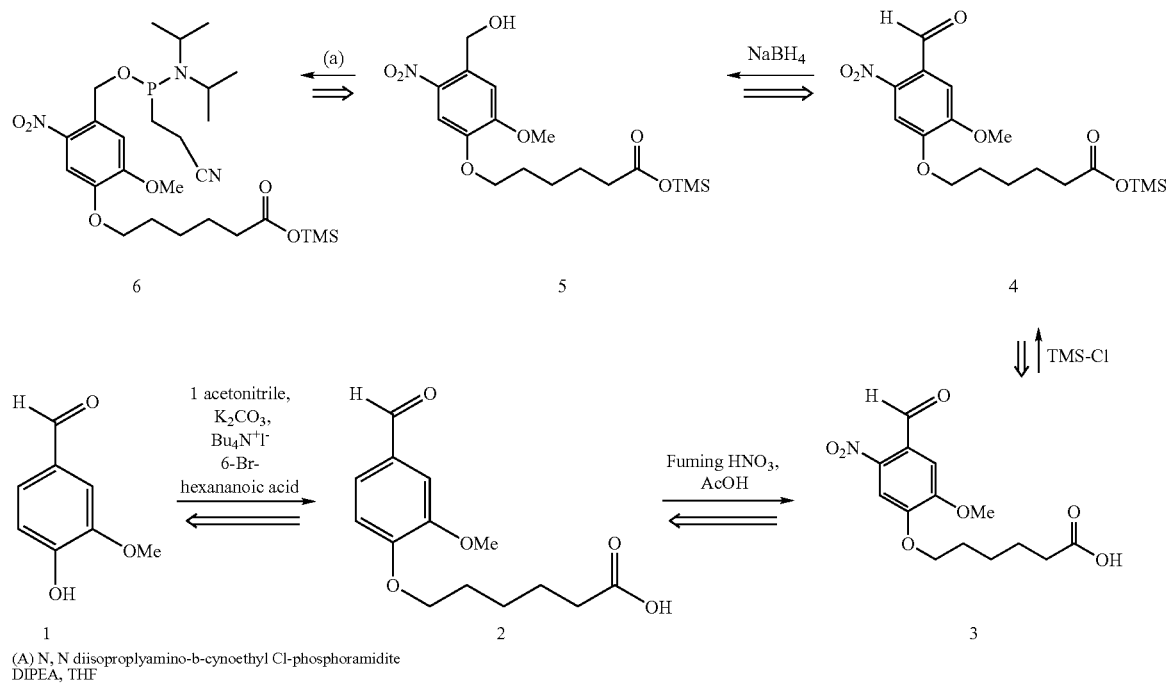

(A) N,N diisoproplyamino-b-cynoethyl Cl-phosphoramidite
DIPEA, THF

Standard peptide coupling using BOP reagent to activate the carboxyl group, will allow the peptide to be attached under mild conditions. To cleave and release the bar code at the appropriate time, UV light at 365–400 nm will be illuminated on the compound. The reaction scheme is presented below in scheme 2

Scheme 2

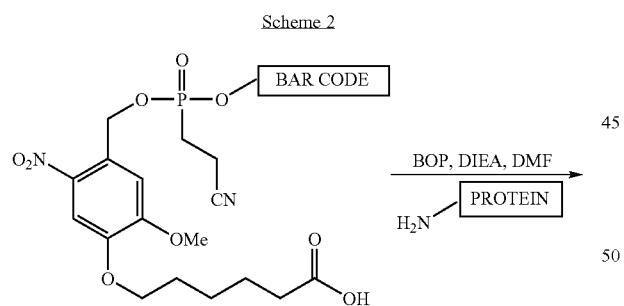

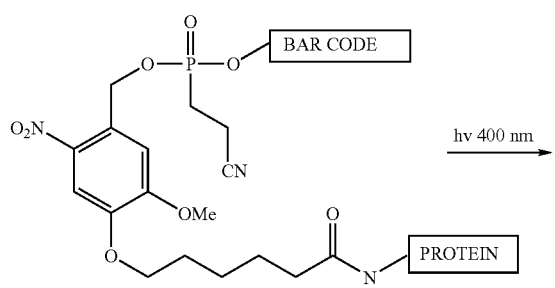

-continued

The proposed mechanism for photolysis of o-nitrobenzyl carbonate ester is present in the literature, but no specific mechanism for the photolysis of the corresponding phosphodiester is presented. Therefore, in scheme 3, the mechanism for a carbonate ester is shown. The mechanism for the phosphodiester should resemble the carbonate.

Scheme 3

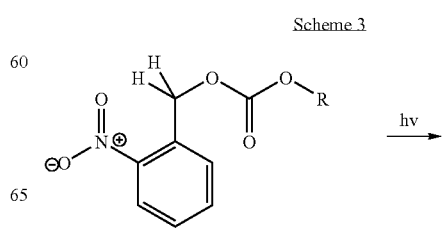

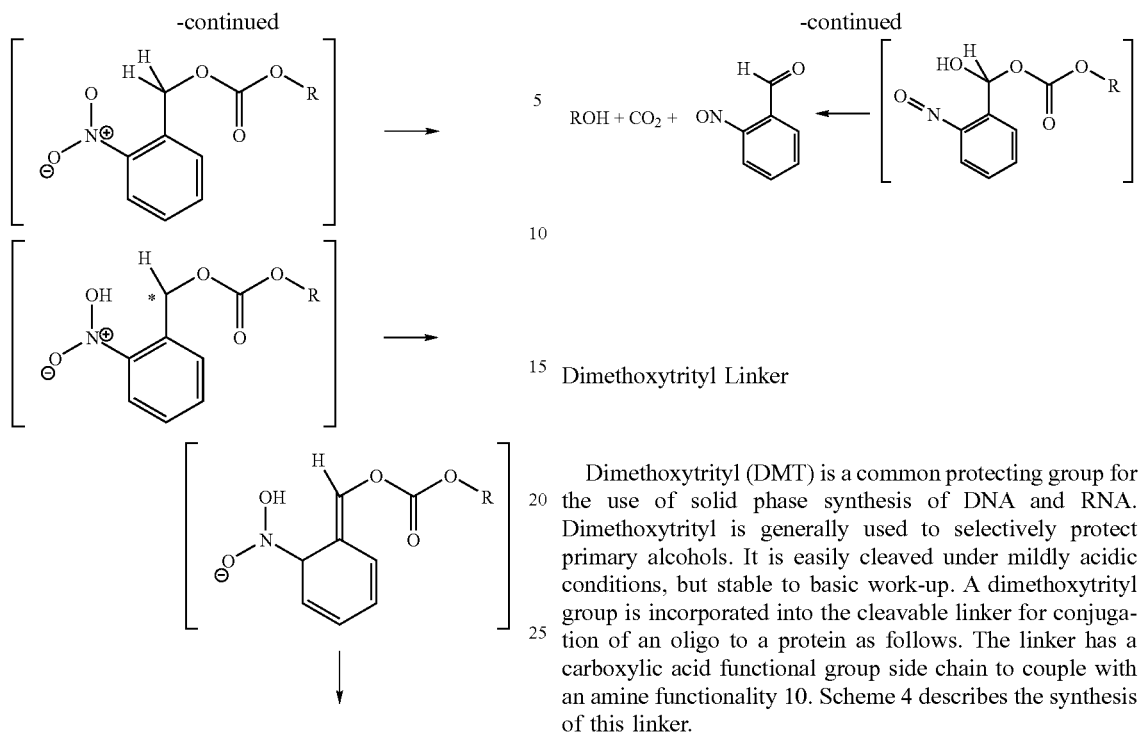

Dimethoxytrityl Linker

Dimethoxytrityl (DMT) is a common protecting group for the use of solid phase synthesis of DNA and RNA. Dimethoxytrityl is generally used to selectively protect primary alcohols. It is easily cleaved under mildly acidic conditions, but stable to basic work-up. A dimethoxytrityl group is incorporated into the cleavable linker for conjugation of an oligo to a protein as follows. The linker has a carboxylic acid functional group side chain to couple with an amine functionality 10. Scheme 4 describes the synthesis of this linker.

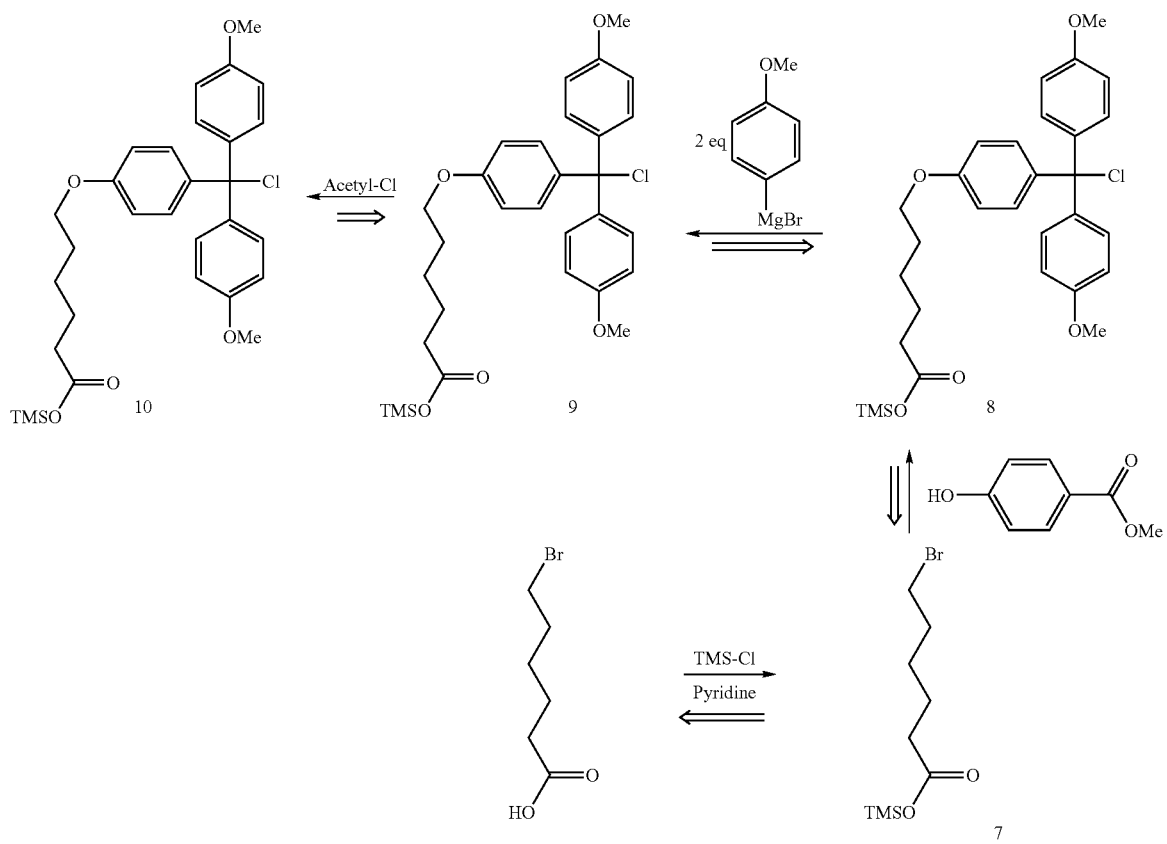

6-Bromohexanoic acid may be protected, where desired, prior to coupling with the phenol. If it is protected with TMS, it yields 7 the silyl ester of 6-bromohexanoic acid. 7 then alkylates p-hydroxy methylbenzoate to yield 8. 7 behaves like the methyl ester during Grignard reaction. If alkylation at the silyl ester occurs, it is necessary to reverse the addition order and form the tertiary alcohol before alkylating with the 6-Bromohexanoic acid. The next step involves a double Grignard reaction at the ester, yielding alcohol 9. If the TMS protection of the caboxylate is not necessary, three equivalents of the Grignard will be necessary. The tertiary alcohol is then substituted with Cl using acetyl-Cl, converting the compound to the linker/protecting group 10. This halide is then coupled to a primary alcohol using the same procedure as DMT protection. Once coupled to an oligo, the DMT linker is then attached to an amine functionality using standard peptide coupling techniques. Treatment with trichloroacetic acid is the standard deprotection method for DMT. The linker is more labile than the DMT because it has three electron donating groups vs. the two on DMT, so a milder acid treatment cleaves it readily. The general scheme is listed below.

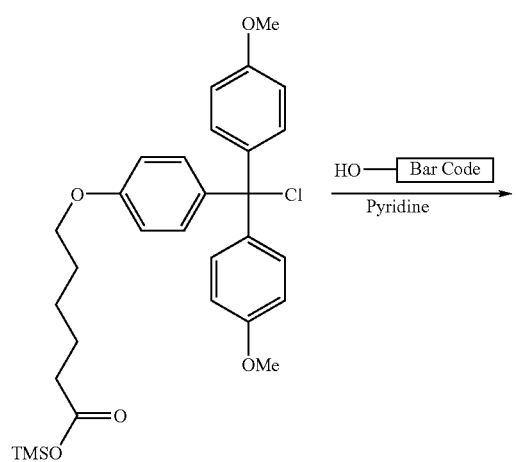

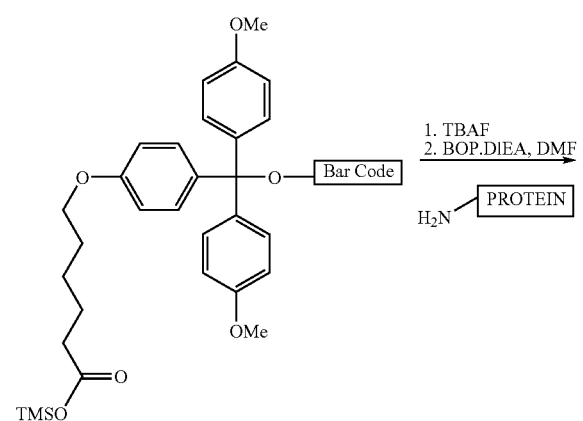

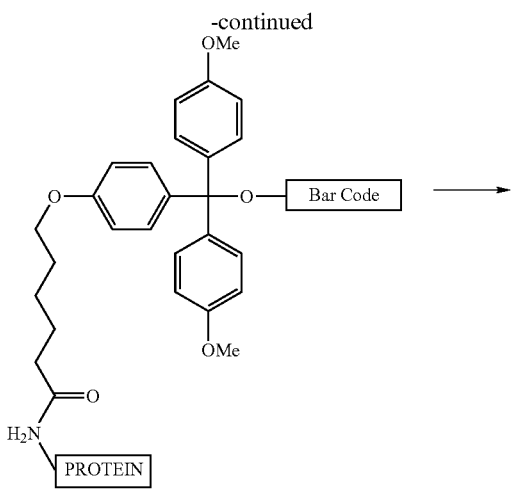

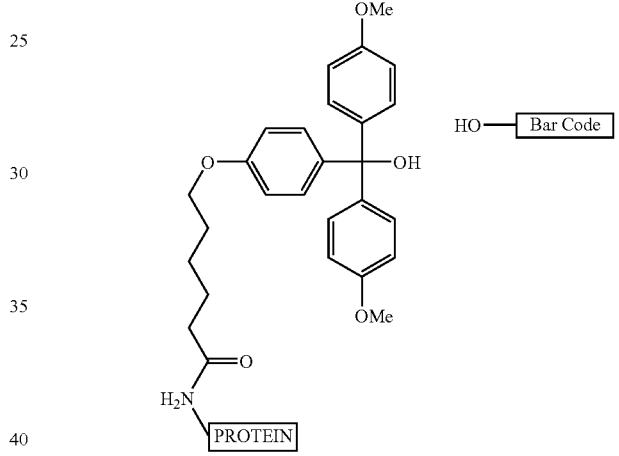

It is evident from the above results and discussion that the subject targeted molecular bar codes constitute a significant advance in the field of analyte detection. The subject bar codes can be read directly without amplification and labeling steps. Furthermore, the bar codes can be read rapidly in much shorter times than that required for methods in which other labels, such as fluorescent or radioactive labels, are employed. In addition, the labels can be read from a heterogeneous population and need not be isolated before being read.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for detecting the presence of an analyte in a sample, said method comprising:
   (a) contacting said sample with at least one targeted molecular bar code under conditions sufficient for a specific binding pair to bind to said analyte in said sample, wherein said molecular bar code comprises:
      (i) a charged polymer capable of generating a reproducible signal upon passage through a nanopore; and
      (ii) a member of a specific binding pair, wherein said specific binding pair member is joined directly or through a linking group to said molecular bar code;
   (b) separating unbound targeted molecular bar code from analyte-bound targeted molecular bar code;
   (c) treating said analyte bound targeted molecular bar code in a manner sufficient to release said molecular bar code from said analyte-bound targeted molecular bar code and produce free molecular bar code;
   (e) detecting the presence of said free molecular bar code by translocating said free molecular bar code through a nanopore; and
   (f) relating the presence of said free molecular bar code to the presence of said analyte in said sample.

2. The method according to claim 1, wherein said detecting step further comprises observing a current blockade effect of said translocation on said nanopore.

3. The method according to claim 1, wherein said method comprises contacting a plurality of different targeted molecular bar codes with said sample.

4. The method according to claim 3, wherein said sample size does not exceed the size of a biological cell.

5. The method according to claim 1, wherein said charged polymer is negatively charged.

6. The method according to claim 5, wherein said negatively charged polymer is made up of monomeric units that comprise a moiety selected from the group consisting of a phosphate group or a phosphorothioate group.

7. The method according to claim 5, wherein said polymer is a block copolymer of a plurality of blocks, wherein said plurality of blocks are selected from two or more different blocks.

8. The method according to claim 7, wherein said block copolymer comprises three different blocks.

9. The method according to claim 5, wherein said molecular bar code comprises a linking group.

10. The method according to claim 9, wherein said linking group is a photocleavable linking group.

11. A method for detecting the presence of an analyte in a sample, said method comprising:
   (a) contacting said sample with at least one targeted molecular bar code under conditions sufficient for a specific binding pair to bind to said analyte in said sample, wherein said molecular bar code comprises:
      (i) a negatively charged block copolymer of from one to twenty blocks, wherein said blocks are selected from two or more different blocks, wherein each block consists of monomeric units comprising a phosphate group; and
      (ii) a member of a specific binding pair, wherein said member of a specific binding pair is joined to said negatively charged block copolymer through a linking group;
   (b) separating unbound targeted molecular bar code from analyte-bound targeted molecular bar code;
   (c) treating said analyte bound targeted molecular bar code in a manner sufficient to release said molecular bar code from said analyte-bound targeted molecular bar code and produce free molecular bar code;
   (e) detecting the presence of said free molecular bar code; and
   (f) relating the presence of said free molecular bar code to the presence of said analyte in said sample.

12. The method according to claim 11, wherein said detecting step comprises translocating said free molecular bar code through a nanopore, thereby producing a signal.

13. The method according to claim 12, wherein said detecting step further comprises observing a current blockade effect of said translocation on said nanopore.

14. The method according to claim 11, wherein said method comprises contacting a plurality of different targeted molecular bar codes with said sample.

15. The method according to claim 14, wherein said sample size does not exceed the size of a biological cell.

16. The method according to claim 11, wherein said blocks are selected from two to four different blocks.

17. The method according to claim 11, wherein each block is a homopolymer of monomeric units selected from the group consisting of phosphates and sugar phosphates.

18. The method according to claim 11, wherein said sugar phosphates are selected from the group consisting of ribose phosphates and deoxyribose phosphates.

19. The method according to claim 18, wherein said sugar phosphates may optionally comprise a heterocyclic nitrogenous base.

20. The method according to claim 19, wherein said heterocyclic nitrogenous base is a purine or a pyrimidine.

21. The method according to claim 11, wherein the length of each block of said block copolymer ranges from 15 to 25 nm.

22. The method according to claim 21, wherein said linker is a photocleavable linker.

23. A method for detecting the presence of an analyte in a sample, said method comprising:
   (a) contacting said sample with at least one targeted molecular bar code under conditions sufficient for a specific binding pair to bind to said analyte in said sample, wherein said molecular bar code comprises:
      (i) a negatively charged block copolymer of from two to twenty blocks, wherein said blocks are selected from a group of three different blocks, wherein each block is a homopolymer of monomeric units selected from the group consisting of polyphosphates, oligonucleotides, oligodeoxyribosephosphates, and polyethylene glycol-phosphodiesters; and
      (ii) a member of a specific binding pair, wherein said member of a specific binding pair is joined to said negatively charged block copolymer through a linking group;
   (b) separating unbound targeted molecular bar code from analyte-bound targeted molecular bar code;
   (c) treating said analyte bound targeted molecular bar code in a manner sufficient to release said molecular bar code from said analyte-bound targeted molecular bar code and produce free molecular bar code;
   (e) detecting the presence of said free molecular bar code; and
   (f) relating the presence of said free molecular bar code to the presence of said analyte in said sample.

24. The method according to claim 23, wherein said detecting step comprises translocating said free molecular bar code through a nanopore, thereby producing a signal.

25. The method according to claim 24, wherein said detecting step further comprises observing a current blockade effect of said translocation on said nanopore.

26. The method according to claim 23, wherein said method comprises contacting a plurality of different targeted molecular bar codes with said sample.

27. The method according to claim 26, wherein said sample size does not exceed the size of a biological cell.

28. The method according to claim 23, wherein said three different blocks are: polyethylene glycol-phosphodiesters; oligodeoxyribosephosphates; and oligonucleotides modified to prevent Watson-Crick base pairing.

* * * * *